United States Patent [19]

Earls et al.

[11] Patent Number: 5,227,452
[45] Date of Patent: Jul. 13, 1993

[54] CURABLE MIXTURES OF MESOGENIC EPOXY RESINS AND MESOGENIC POLYAMINES AND CURED COMPOSITIONS

[75] Inventors: Jimmy D. Earls; Robert E. Hefner, Jr.; Paul M. Puckett, all of Lake Jackson, Tex.

[73] Assignee: The Dow Chemical Company, Midland, Mich.

[21] Appl. No.: 906,088

[22] Filed: Jun. 29, 1992

Related U.S. Application Data

[63] Continuation-in-part of Ser. No. 562,182, Aug. 3, 1990, abandoned.

[51] Int. Cl.$^5$ .................. C08G 59/00; C08G 65/08; C08G 65/14
[52] U.S. Cl. ............................. 528/96; 528/97; 528/98; 528/99; 528/100; 528/101; 528/103; 528/104; 528/107; 525/481; 525/482; 525/483; 525/484; 525/523; 525/524; 525/525; 525/526; 528/109; 528/110; 528/111; 528/116; 528/117; 528/118; 528/122; 528/123; 528/124; 528/407

[58] Field of Search .............. 528/96, 97, 98, 99, 528/100, 101

[56] References Cited

U.S. PATENT DOCUMENTS

| | | | |
|---|---|---|---|
| 3,383,360 | 5/1968 | Harrison | 528/99 |
| 3,408,407 | 10/1968 | Cotter et al. | 528/98 |
| 4,762,901 | 9/1988 | Dhein et al. | 528/100 |
| 5,093,471 | 3/1992 | West | 528/418 |

Primary Examiner—John C. Bleutge
Assistant Examiner—Frederick Krass

[57] ABSTRACT

Compositions comprising epoxy resins containing one or more rodlike mesogenic moieties per molecule are cured with polyamines containing one or more rodlike mesogenic moieties per molecule. These curable compositions can be oriented by the application of an electric field or magnetic field or drawing and/or shear flow prior to and/or during curing. The resultant cured products exhibit an improvement in one or more physical and/or mechanical and/or thermal properties as compared to a like epoxy resin system which does not contain any rodlike mesogenic moieties.

29 Claims, No Drawings

CURABLE MIXTURES OF MESOGENIC EPOXY RESINS AND MESOGENIC POLYAMINES AND CURED COMPOSITIONS

CROSS-REFERENCE TO RELATED APPLICATION

This is a continuation-in-part of application Ser. No. 07/562,182 filed Aug. 3, 1990 now abandoned which is incorporated herein by reference in its entirety.

FIELD OF THE INVENTION

The present invention concerns curable (thermosettable) compositions containing one or more mesogenic epoxy resins and one or more mesogenic polyamines, as well as the cured compositions thereof.

BACKGROUND OF THE INVENTION

Epoxy resins are a well established class of curable (thermosettable) compositions which find utility in a myriad of applications. The curing of epoxy resins is effected by a wide range of curing agent, for example, the primary and secondary polyamines including the aliphatic amines, cycloaliphatic amines and aromatic amines; dicarboxylic acids and anhydrides thereof; aromatic hydroxyl containing compounds; imidazoles; guanidines; urea-aldehyde resins, melamine-aldehyde resins and alkoxylated derivatives thereof; amidoamines, and various combinations thereof. In many of the applications served by epoxy resins, it would be desirable to improve one or more of the physical and/or mechanical and/or thermal properties of the cured products.

Corley et al. in U.S. Pat. No. 4,791,154 (issued Dec. 13, 1988) discloses the use of aromatic azopolyamine curing agents with epoxy resins. A compound included as an azopolyamine curing agent is

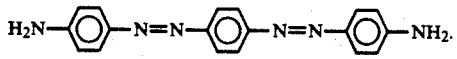

while the diglycidyl ether of 4,4'-dihydroxydiphenyl is included as one of the epoxy resins suitable for use.

Dhein et al. in U.S. Pat. No. 4,762,901 (issued Aug. 9, 1988) discloses the preparation of polymeric networks having superstructures via polymerization of liquid crystalline materials within the liquid crystalline temperature range of said materials. Certain specific epoxy resins and certain specific diamines containing a liquid crystalline moiety are described in the teachings, with a specific example of the glycidyl ether of 4'-hydroxyphenyl-4-hydroxybenzoate cured with 4'-aminophenyl-4-aminobenzoate being disclosed.

The present invention provides a method for improving one or more of the physical and/or mechanical and/or thermal properties of cured epoxy resins by incorporation one or more specific rodlike mesogenic structures into the epoxy resin and one or more of any rodlike mesogenic structures into the polyamine curing agent used therewith. These epoxy resin and polyamine curing agent compositions exhibit ordering of the molecular chains in the melt phase. This morphology is susceptible to flow induced orientation during processing which can result in enhanced unidirectional mechanical properties. This is not possible to any extent with conventional (non-mesogenic) epoxy resin and curing agent compositions. The simultaneous presence of rodlike mesogenic moieties in the epoxy resin as well as the polyamine curing agent allows for a greater concentration of said moieties in the cured products thereof and thus a higher susceptibility to induced orientation.

SUMMARY OF THE INVENTION

One aspect of the present invention pertains to curable (thermosettable) compositions comprising (A) one or more epoxy resins containing one or more rodlike mesogenic moieties represented by the following Formula I

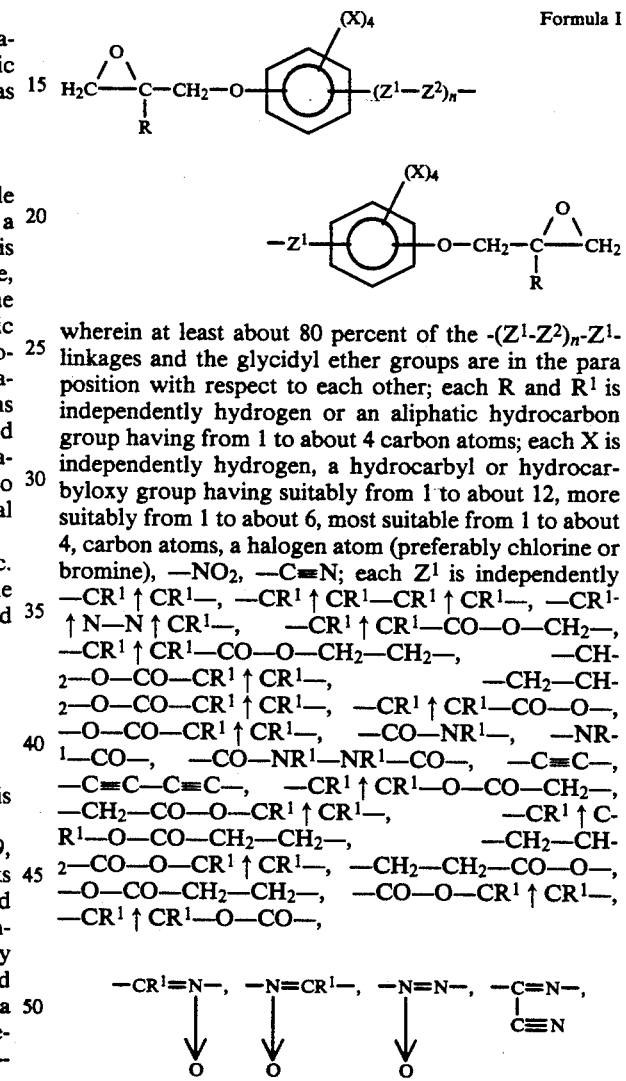

wherein at least about 80 percent of the $-(Z^1-Z^2)_n-Z^1-$ linkages and the glycidyl ether groups are in the para position with respect to each other; each R and $R^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitable from 1 to about 4, carbon atoms, a halogen atom (preferably chlorine or bromine), $-NO_2$, $-C\equiv N$; each $Z^1$ is independently $-CR^1\uparrow CR^1-$, $-CR^1\uparrow CR^1-CR^1\uparrow CR^1-$, $-CR^1\uparrow N-N\uparrow CR^1-$, $-CR^1\uparrow CR^1-CO-O-CH_2-$, $-CR^1\uparrow CR^1-CO-O-CH_2-CH_2-$, $-CH_2-O-CO-CR^1\uparrow CR^1-$, $-CH_2-CH_2-O-CO-CR^1\uparrow CR^1-$, $-CR^1\uparrow CR^1-CO-O-$, $-O-CO-CR^1\uparrow CR^1-$, $-CO-NR^1-$, $-NR^1-CO-$, $-CO-NR^1-NR^1-CO-$, $-C\equiv C-$, $-C\equiv C-C\equiv C-$, $-CR^1\uparrow CR^1-O-CO-CH_2-$, $-CH_2-CO-O-CR^1\uparrow CR^1-$, $-CR^1\uparrow CR^1-O-CO-CH_2-CH_2-$, $-CH_2-CH_2-CO-O-CR^1\uparrow CR^1-$, $-CH_2-CH_2-CO-O-$, $-O-CO-CH_2-CH_2-$, $-CO-O-CR^1\uparrow CR^1-$, $-CR^1\uparrow CR^1-O-CO-$,

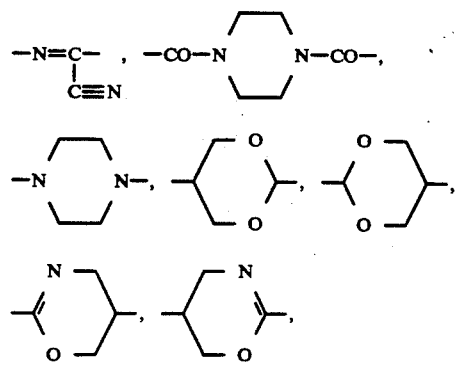

-continued

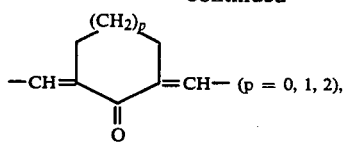
(p = 0, 1, 2),

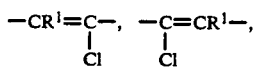

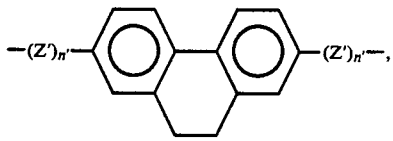

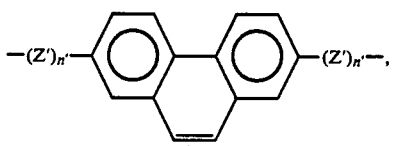

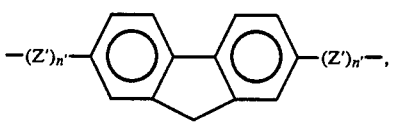

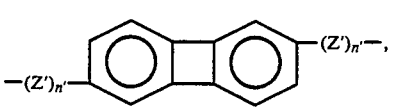

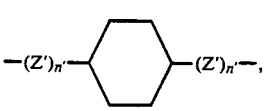

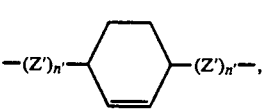

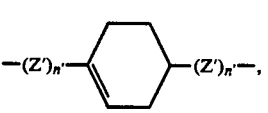

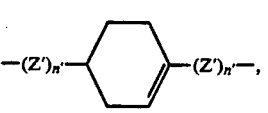

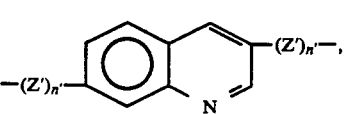

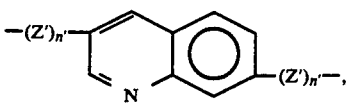

-continued

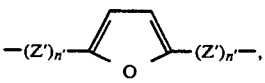

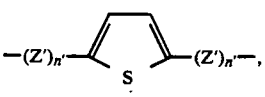

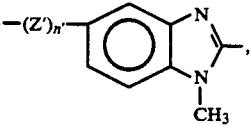

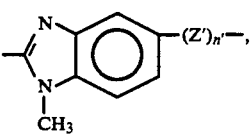

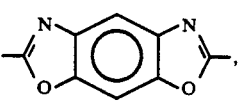

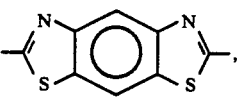

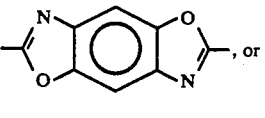, or

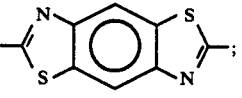;

$Z^2$ is a group represented by a cyclic or bicyclic ring system containing from 5 to about 12 carbon atoms and may be cycloaliphatic, polycycloaliphatic, aromatic or combination thereof; n is 0 to 2; each Z' is independently a —CO—, —O—CO—, —CO—O—, —CO—NR$^1$—, or —NR$^1$—CO— group and each n' independently has a value of zero or one;

with the proviso that:
(a) both of the R$^1$ groups in the —CR$^1$=CR$^1$— group cannot simultaneously be a hydrogen atom;
(b) each $Z^1$ can also independently be

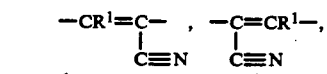

—CR$^1$=N—, —N=CR$^1$—, —CO—CR$^1$=CR$^1$— and —CR$^1$=CR$^1$—CO— when $Z^2$ is not a benzene ring and n≠0;

(c) R$^1$ in the —CR$^1$=N— and —N=CR$^1$— groups is other than hydrogen;

(d) when n=1, either one of $Z^1$ can also be selected from the group consisting of —CH=CH—, —N'N—, —CO—S—, —S—CO—, —CH=N—, —N'CH—, —O—CO—, —CO—O— and a direct single bond provided that the other $Z^1$ group is not selected from this same group or it not selected from the group selected from the group consisting of

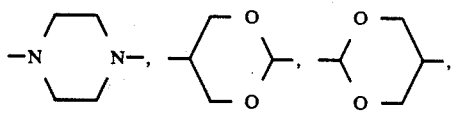

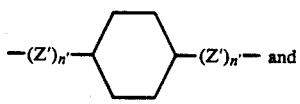 and when (i) each n' is zero, or (ii) when one n'=zero and one n'=1 with Z' being —O—CO— or —CO—O— and $R^1$ is a group having only one carbon atom;

(e) when n=2, one or two $Z^1$ groups can also independently be selected from the group consisting of —CH=CH—, —N=N—, —CO—S—, —S—CO—, —CH=N—, —N=CH—, —O—CO—, —CO—O—, and a direct single bond, provided that the remaining $Z^1$ groups are not selected from this group;

(f) when one $Z^1$ is

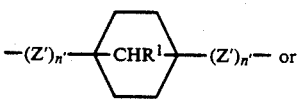

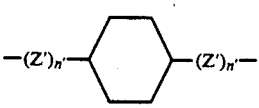

wherein (i) when each n'=1 with each Z' being —O—CO— or —CO—O—, or (ii) when one n'=1 with Z' being —O—CO— or —CO—O— and the other n'=zero resulting in the other Z' being a direct bond and $R^1$ is a group having only one carbon atom, then n must have a value of 1 or 2 and $R^1$ is a group having only one carbon atom; or by the following Formula II

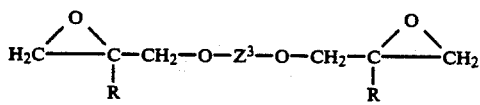

wherein $Z^3$ is

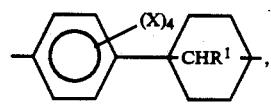

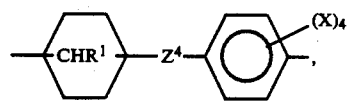

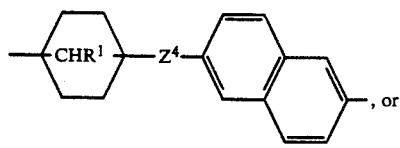

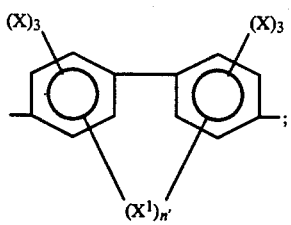

and $Z^4$ is —CO—O—, —O—CO—, —$NR^1$—CO— or —CO—$NR^1$—; $X^1$ is a divalent hydrocarbyl group having from 1 to about 10, preferably from 1 to about 4, carbon atoms which can contain one or more heteroatoms selected from N, O or S and may be saturated or unsaturated; each R and $R^1$ is independently hydrogen or an aliphatic hydrocarbon group having from 1 to about 4 carbon atoms; each X is independently hydrogen, a hydrocarbyl or hydrocarbyloxy group having suitable from 1 to about 12, more suitably from 1 to about 6, most suitably from 1 to about 4, carbon atoms, a halogen atom (preferably chlorine or bromine), —$NO_2$, or —C≡N; and n' is zero or one; and with the proviso that $Z^4$ is not —CO—O— or —O—CO— when $R^1$ is a group having only one carbon atom; and (B) a curing amount of one or more polyamines containing one or more rodlike mesogenic moieties.

Another aspect of the present invention pertains to curable compositions comprising (A) one or more advanced epoxy resins prepared by reacting (1) one or more of the epoxy resins containing one or more rodlike mesogenic moieties, said epoxy resin being those represented by either the following Formula I

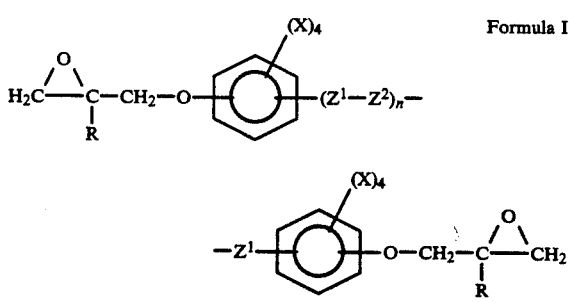

Formula I wherein at least about 80 percent of the —($Z^1$—$Z^2$)$_n$—$Z^1$— linkages and the glycidyl ether groups are in the para position with respect to each other; each R and $R^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —$NO_2$, or —C≡N; each $Z^1$ is independently —$CR^{1'}CR^1$—, —$CR^1$=$CR^1$—$CR^1$=$CR^1$—, —$CR^1$=N—N=$CR^1$—, —$CR^1$=$CR^1$—CO —O—CH₂—, —CR¹=CR¹—CO—O—CH₂—CH₂—, —CH₂—O—CO—CR¹=CR¹—, —CH₂—CH₂—O—CO—CR¹=CR¹—, —CR¹=CR¹—CO—O—, —O—CO—CR¹=CR¹—, —CO—NR¹—, —NR¹—CO—, —CO—NR¹—NR¹—CO—, —C≡C—, —C≡C—C≡C—, —N=N—, —CO—S—, —S—CO—, —CR¹=CR¹—O—CO—CH₂—, —CH₂—CO—O—CR¹=CR¹—, —CR¹=CR¹—O—CO—CH₂—CH₂—, —CH₂—CH₂—CO—O—CR¹=CR¹—, —CH₂—CH₂—CO—O—, —O—CO—CH₂—CH₂—, —CO—O—CR¹=CR¹—, —CR¹=CR¹—O—CO—, a direct single bond when n≧1,
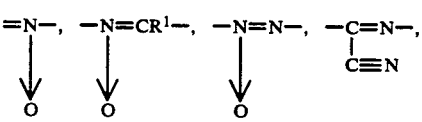
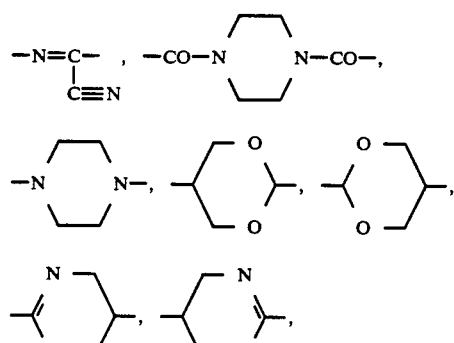
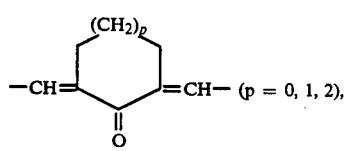
—CR¹=C—, —C=CR¹—,
    |         |
    Cl       Cl
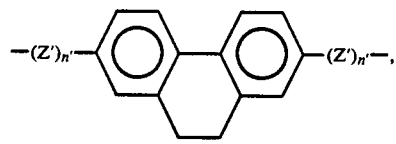
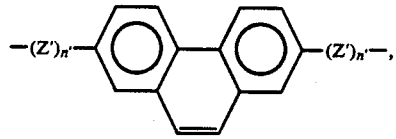
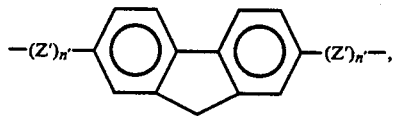
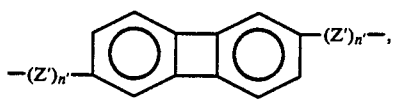
-continued
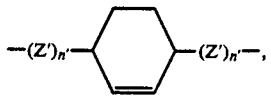
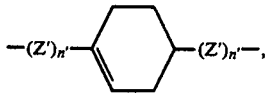
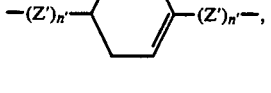
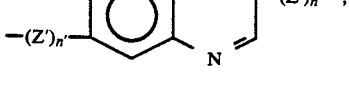
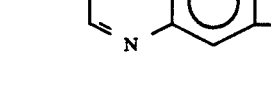
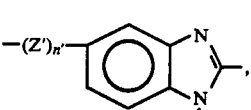
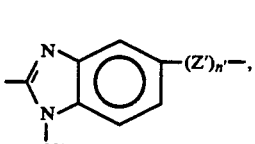
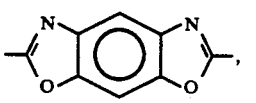
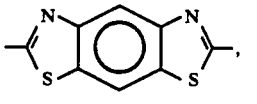

-continued

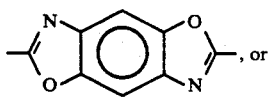, or

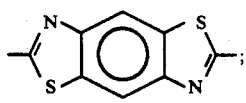;

Z² is a group represented by a cyclic or bicyclic ring system containing from 5 to about 12 carbon atoms and may be cycloaliphatic, polycycloaliphatic, aromatic or a combination thereof; n is 0 to 2; each Z' is independently a —CO—, —O—CO—, —CO—O—, —CO—NR¹—, or —NR¹—CO— group and each n' independently has a value of zero or one; with the proviso that each Z¹ can also independently be

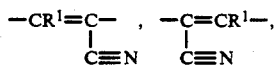

—CR¹=N—, —N=CR¹—, —CO—CR¹=CR¹—, —CR¹=CR¹—CO—, —CO—O—, and —O—CO— when Z² is not a benzene ring and when n≠0; or the following formula II

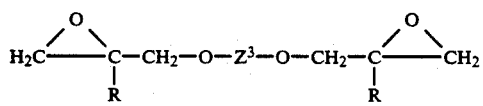

wherein Z³ is

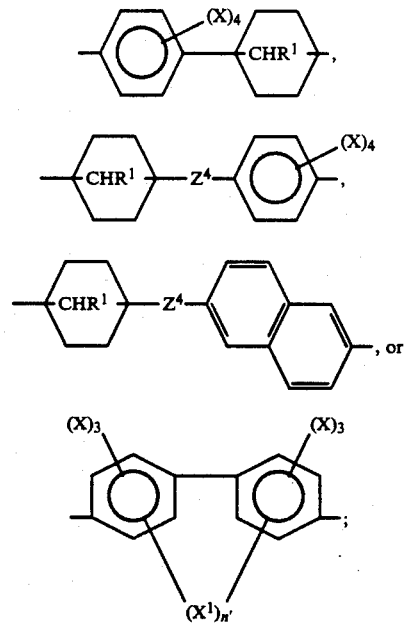

and Z⁴ is —CO—O—, —O—CO—, —NR¹—CO— or —CO—NR¹—; X¹ is a divalent hydrocarbyl group having from 1 to about 10, preferably from 1 to about 4, carbon atoms which can contain one or more heteroatoms selected from N, O or S and may be saturated for unsaturated; each R and R¹ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO₂, or —C▷N; and n' is zero or one; with (2) at least one compound having an average of more than one active hydrogen atom per molecule; and wherein components (1) and (2) are employed in quantities which provide a ratio of active hydrogen atoms per epoxide group of from about 0.01:1 to about 0.95:1, more suitably from about 0.05:1 to about 0.8:1, most suitably from about 0.1:1 to about 0.5:1; and (B) a curing amount of one or more polyamines containing one or more rodlike mesogenic moieties.

Another aspect of the present invention pertains to curable compositions comprising (A) one or more of the epoxy resins or monoepoxide compounds containing one or more rodlike mesogenic moieties which epoxy resins or ionoepoxide compounds are represented by the aforementioned Formulas I or II or by the following Formulas III or IV

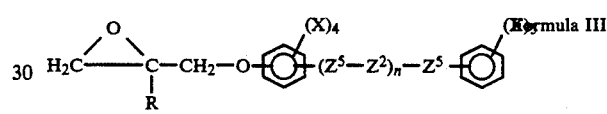

wherein at least about 80 percent of the —(Z⁵—Z²—)ₙ—Z⁵— linkages and the glycidyl ether groups are in the para position with respect to each other; each R and R¹ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO₂, or —C≡N; each Z⁵ is independently —CR¹=CR¹—, —CR¹=CR¹—CR¹=C-R¹—, —CR¹=N—N=CR¹—, —CR¹=C-R¹—CO—O—CH₂—, —CR¹=CR¹—CO—O—CH₂—CH₂—, —CH₂—O—CO—CR¹=CR¹—, —CH₂—CH₂—O—CO—CR¹=CR¹—, —CR¹=C-R¹—CO—O—, —O—CO—CR¹=CR¹—, —N=N—, —CO—NR¹—, —NR¹—CO—, —CO—NR¹—NR¹—CO—, —C≡C—, —C≡C—C≡C—, —CO—S—, —S—CO—, —CR¹=N—, —N=CR¹—, —CO—O—, —O—CO—, —CR¹=CR¹—O—CO—CH₂—, —CH₂—CO—O—CR¹=CR¹—, —CR¹=C-R¹—O—CO—CH₂—CH₂—, —CH₂—CH₂—CO—O—CR¹=CR¹—, —CH₂—CH₂—O—CO—CH₂—CH₂—, —CH₂—CH-₂—CO—O—CR¹=CR¹³, —CH₂—CH₂—CO—O—, —O—CO—CH₂—CH₂—, —CO—O—CR¹=CH¹—, —CR¹=CR¹—O—CO—, a direct single bond when n≧1,

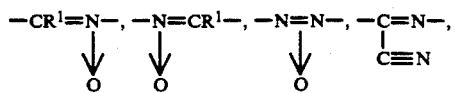

-continued
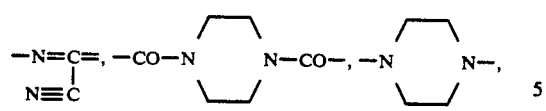
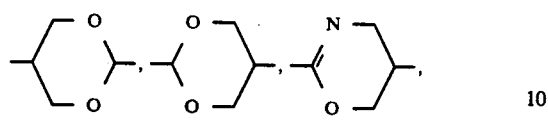
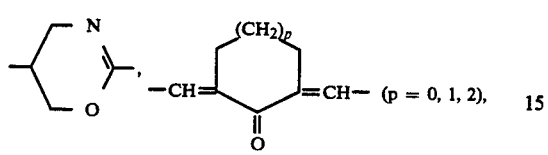
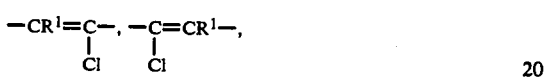
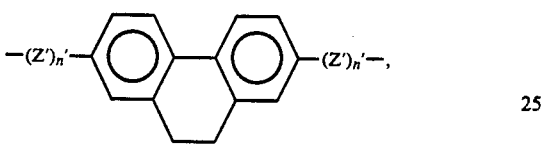
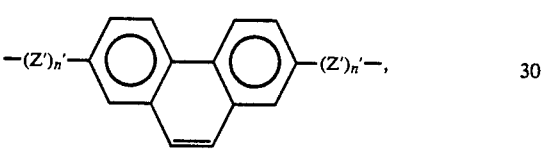
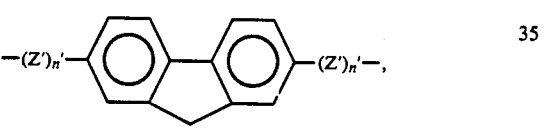
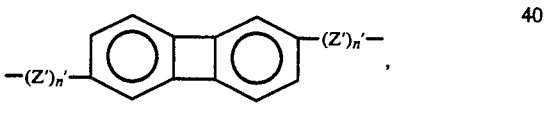
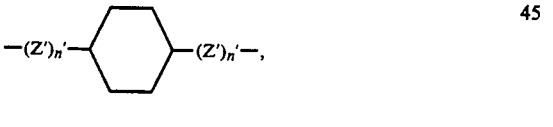
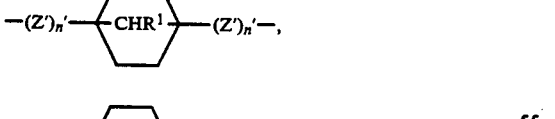
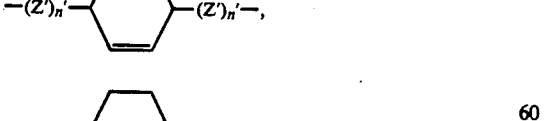
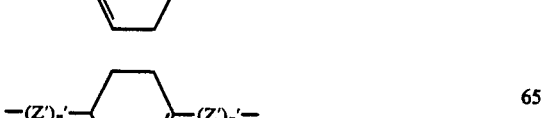
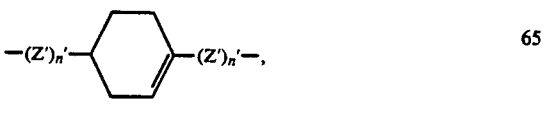
-continued
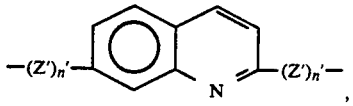
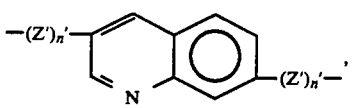
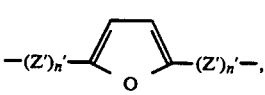
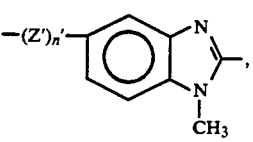
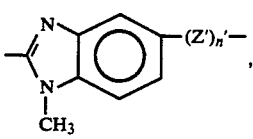
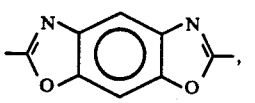
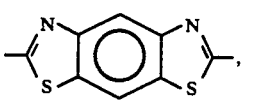
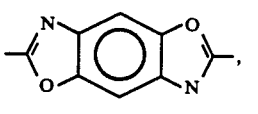
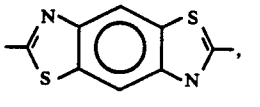
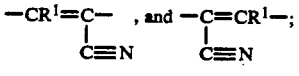
$Z^2$ is a group represented by a cyclic or bicyclic ring system containing from 5 to about 12 carbon atoms and may be cycloaliphatic, polycycloaliphatic, aromatic or a combination thereof; n is zero or two; each Z' is independently a —CO—, —O—CO—, —CO—O—, —CO—NR$^1$—, or —NR$^1$—CO— group; and each n' is independently zero or one; or the following Formula IV

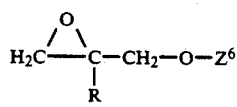

Formula IV wherein $Z^6$ is

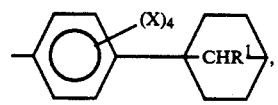

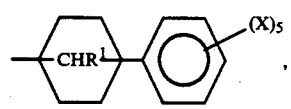

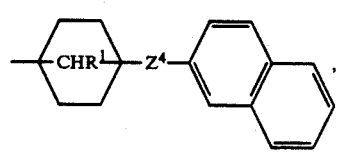

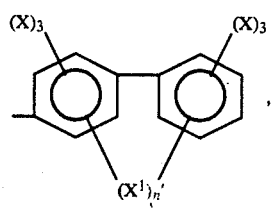

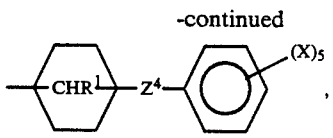

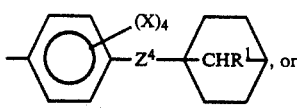

, or

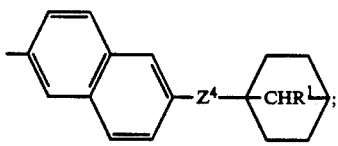

;

and $Z^4$ is —CO—O—, —O—CO—, —NR$^1$—CO—, or —CO—NR$^1$—; each R and $R^1$ is independently hydrogen or an aliphatic hydrocarbon group having from 1 to about 4 group atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; $X^1$ is a divalent hydrocarbyl group having from 1 to about 10, preferably from 1 to about 4, carbon atoms which can contain one or more heteroatoms selected from N, O or S and may be saturated or unsaturated; and n' is zero or one; and (B) one or more polyepoxides represented by the following Formulas V, VI, VII, VIII, IX, X or XI;

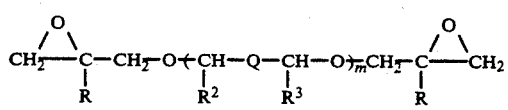

Formula V

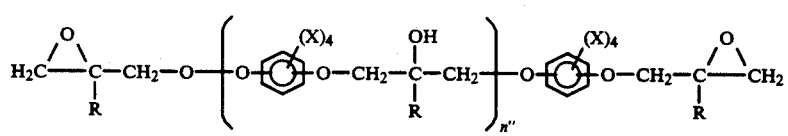

Formula VI

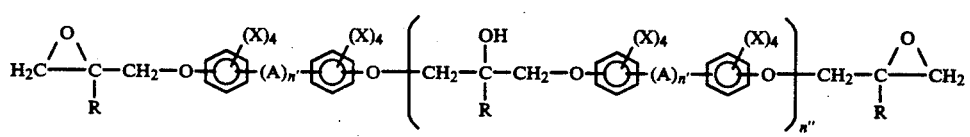

Formula VII

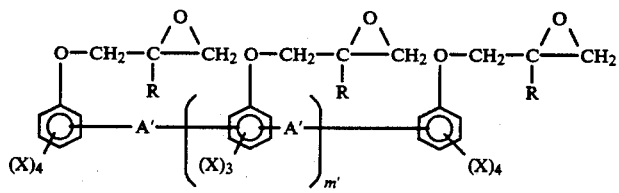

Formula VIII

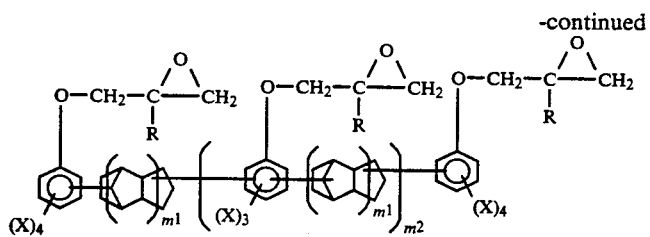

Formula IX

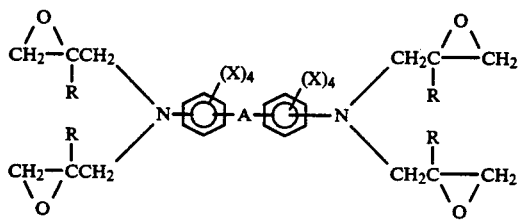

Formula X

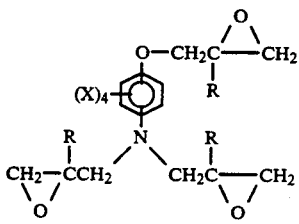

Formula XI wherein each A is independently a divalent hydrocarbyl group having from 1 to about 12, preferably from 1 to about 6, more preferably from 1 to about 3, carbon atoms, —O—, —S—, —S—S—, —SO—, —SO$_2$—, or —CO—; each A' is independently a divalent hydrocarbon group having from 1 to about 6, preferably from 1 to about 3, carbon atoms; Q is a single bond, —CH$_2$—S—CH$_2$—, —(CH$_2$)$_{ni}$—, or

each R is independently hydrogen or an alkyl group having from 1 to about 4 carbon atoms; each $R^2$ and $R^3$ is independently hydrogen, a hydrocarbyl or halohydrocarbyl group having from 1 to about 6, preferably from 1 to about 3, more preferably from 1 to about 2, carbon atoms; each X is independently hydrogen, a hydrocarbyl or hydrocarbyloxy group having from 1 to about 12, preferably from 1 to about 6, most preferably from 1 to about 4, carbon atoms, a halogen atom, —NO$_2$ or C≡N; m has a value from about 1 to about 10, preferably from about 1 to about 4, more preferably from about 1 to about 2; m' has an average value from about 0.01 to about 12, preferably from about 1 to about 6, more preferably from about 1 to about 3, m$^1$ has an average value form about 1 to about 12, preferably from about 1 to about 6, more preferably from about 1 to about 3; m$^2$ has a value from about 1 to about 12, preferably from about 2 to about 6, more preferably from about 2 to about 3; n' has a value of zero of 1; n" has an average value from about zero to about 3, preferably from about zero to about 1.5, more preferably from about zero to about 0.5, and n$^1$ has an average value from about 1 to about 10 and wherein component (A) is present in an amount suitably from about 1 to about 99, more suitably from about 10 to about 80, most suitably from about 10 to about 50, percent by weight based upon the combined weight of components (A) and (B) and component (B) is present in an amount suitably from about 99 to about 1, more suitably from about 90 to about 20, most suitably from about 90 to about 50, percent by weight based upon the combined weight of components (A) and (B); and (C) a curing amount of one or more polyamines containing one or more rodlike mesogenic moieties.

Another aspect of the present invention pertains to curable compositions comprising (A) one or more of the advanced epoxy resins containing one or more rodlike mesogenic moieties which advanced epoxy resins are prepared by reacting one or more epoxy resins represented by Formulas I or II and at least one compound having an average of more than one active hydrogen atom per molecule; and (B) one or more polyepoxides represented by Formulas V, VI, VII, VIII, IX, X or XI; and wherein component (A) is present in an amount suitably from about 1 to about 99, more suitably from about 10 to about 80, most suitably from about 10 to about 50, percent by weight based upon the combined weight of components (A) and (B) and component (B) is present in an amount suitably from about 99 to about 1, more suitably from about 90 to about 20, most suitably from about 90 to about 50, percent by weight based upon the combined weight of components (A) and (B); and (C) a curing amount of one or more polyamines containing one or more rodlike mesogenic moieties.

Another aspect of the present invention pertains to curable compositions comprising (I) a blend of (A) one or more epoxy resins containing an average of more than one vicinal epoxide group per molecule and one or more rodlike mesogenic moieties per molecule and (B) one or more compounds containing only one vicinal epoxide group per molecule and one or more rodlike mesogenic moieties per molecule and (II) at least one polyamine containing one or more rodlike mesogenic moieties.

A further aspect of the present invention pertains to products resulting from curing the aforementioned curable compositions.

A further aspect of the present invention pertains to products resulting from the application of an electric field or magnetic field or drawing and/or shear flow before and/or during curing or processing of the aforementioned curable compositions.

A further aspect of the present invention pertains to products resulting from curing a curable composition comprising (A) at least one epoxy resin containing one or more rodlike mesogenic moieties, said epoxy resin being represented by the following Formula I

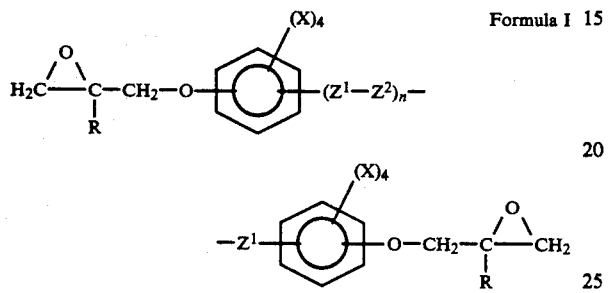

wherein at least about 80 percent of the —($Z^1$—$Z^2$)$_n$—$Z^1$— linkages and the glycidyl ether groups are in the para position with respect to each other; each R and $R^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —$NO_2$, or —C≡N; $Z^2$, $Z'$, n and n' are as hereinbefore defined;

with the proviso that;
(a) when n=1, either one of $Z^1$ is selected from the group consisting of —CH=CH—, —N=N—, —CO—S—, —S—CO—, —CH=N—, —N=CH—, —O—CO—, —CO—O— and a direct single bond provided that the other $Z^1$ group is selected from this same group or is selected from a group selected from the group consisting of

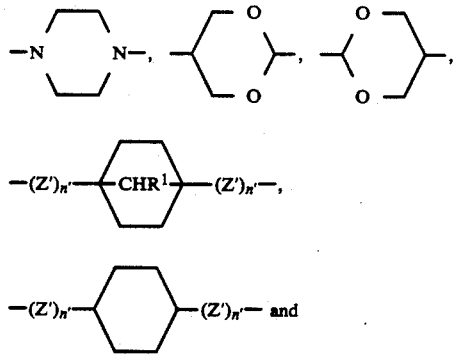

when (i) each n' is zero, or (ii) when one n'=zero and one n'=1 with Z' being —O—CO— or —C—O— and $R^1$ is a group having only one carbon atom;
(b) when n=2, one or two $Z^1$ groups are independently selected from the group consisting of —CH=CH—, —N=N—, —CO—S—, —S—CO—, —CH=N—, —N=CH—, —O—CO—, —CO—O—, and a direct single bond, provided that the remaining $Z^1$ groups are selected from this group;
(c) when one $Z^1$ is

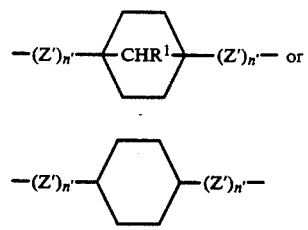

wherein (i) when each n'=1 with each Z' being —O—CO— or —CO—O—, or (ii) when one n'=1 with Z' being —O—CO— or —CO—O— and the other n'=zero resulting in the other Z' being a direct bond and $R^1$ is a group having only one carbon atom, then n must have a value of 1 or 2 and $R^1$ is a group having only one carbon atom; and (B) a curing amount of one or more polyamines containing one or more rodlike mesogenic moieties; and wherein said curing is conducted outside the liquid crystal transition temperature range of said epoxy resin and with the proviso that the epoxy resin and curing agent are not simultaneously the diglycidyl ether of 4,4'-dihydroxyphenylbenzoate and 4,4'-diaminophenylbenzoate, respectively.

A further aspect of the present invention pertains to products resulting from curing a curable composition comprising (A) at least one epoxy resin containing one or more rodlike mesogenic moieties said epoxy resin being represented by the following Formula II

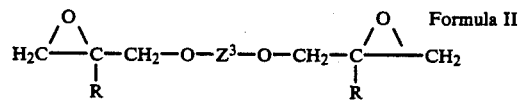

wherein $Z^3$ is

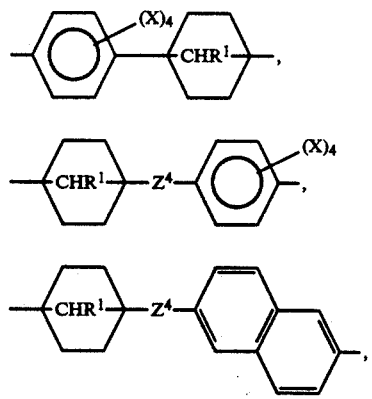

and $Z^4$ is —CO—O—, or —O—CO—; each R is independently hydrogen or an aliphatic hydrocarbon group having from 1 to about 4 carbon atoms; $R^1$ is a group having only one carbon atom; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —$NO_2$, or —C≡N; and (B) a curing amount of one or more polyamines containing one or more rodlike mesogenic moieties; and wherein said curing is conducted outside the liquid crystal transition temperature range of said epoxy resin.

A still further aspect of the present invention pertains to products resulting from the application of an electric field or magnetic field or drawing and/or shear flow before and/or during curing or processing of a curable composition comprising (A) at least one epoxy resin containing one or more rodlike mesogenic moieties said epoxy resin being those represented by either the following Formula I

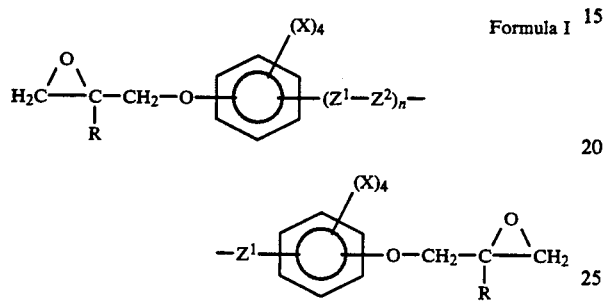

wherein at least about 80 percent of the $-(Z^1-Z^2)_n-Z^1-$ linkages and the glycidyl ether groups are in the para position with respect to each other; each R and $R^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), $-NO_2$, or $-C\equiv N$; each $Z^1$ is independently $-CR^1=CR^1-$, $-CR^1=CR^1CR^1-$, $-CR^1=N-N=CR^1-$, $-CR^1=CR^1-CO-O-CH_2-$, $-CR^1=CR^1-CO-O-CH_2-CH_2-$, $-CH_2-O-CO-CR^1=CR^1-$, $-CH_2-O-CO-CR^1=CR^1-$, $-CR^1=CR^1-CO-O-$, $-O-CO-CR^1=CR^1-$, $-CO-NR^1-$, $-NR^1-CO-$, $-CO-NR^1-NR^1-CO-$, $-C\equiv C-$, $-C\equiv C-C\equiv C-$, $-N=N-$, $-CO-S-$, $-S-CO-$, $-CR^1=N-$, $-N=CR^1-$, $-CO-CR^1=CR^1-$, $-CR^1=CR^1-CO-$, $-CR^1=CR^1-O-CO-CH_2-$, $-CH_2-CO-O-CR^1=CR^1-$, $-CR^1=CR^1-O-CO-CH_2-CH_2-$, $-CH_2-CH_2-CO-O-CR^1=CR^1-$, $-CH_2-CH_2-CO-O-$, $-O-CO-CH_2-CH_2-$, $-CO-O-CR^1=CR^1-$, $-CR^1=CR^1-O-CO-$,

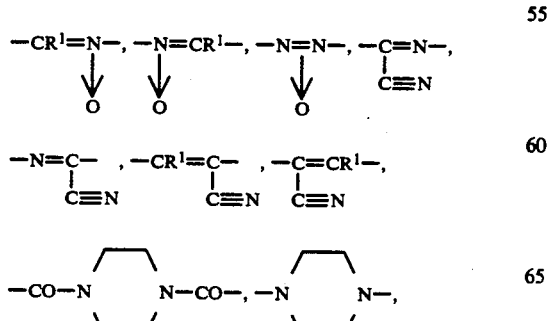

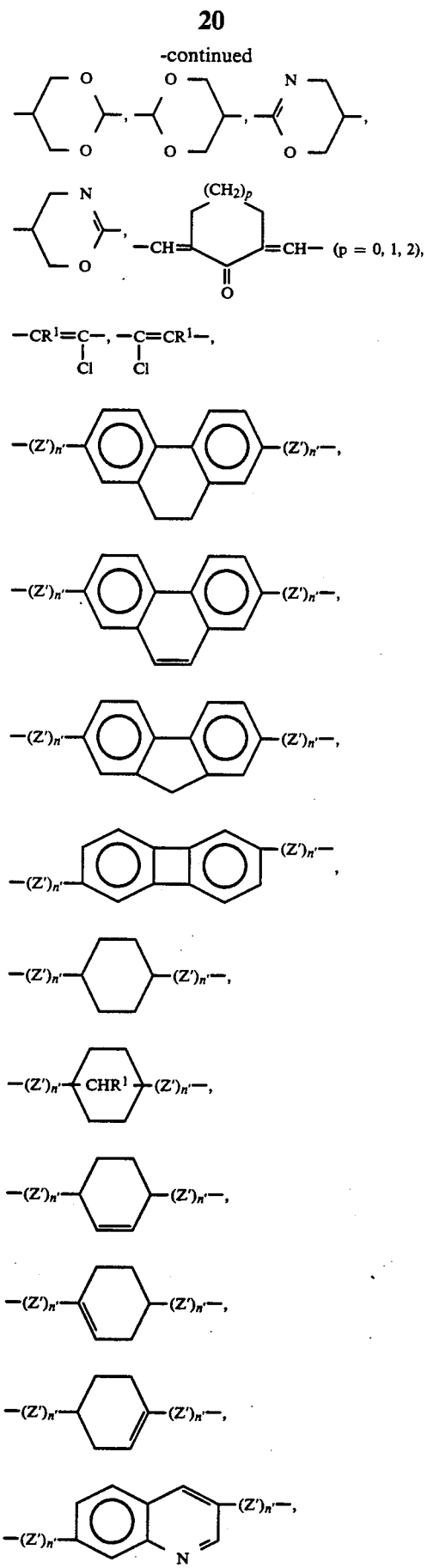

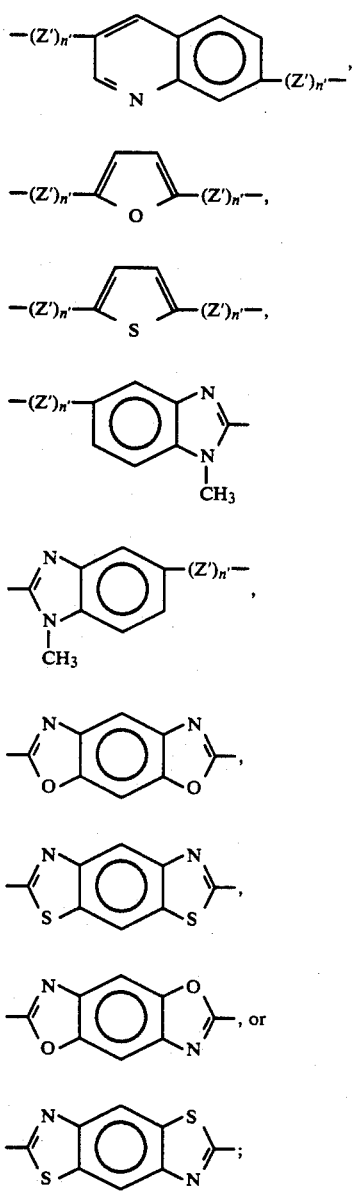

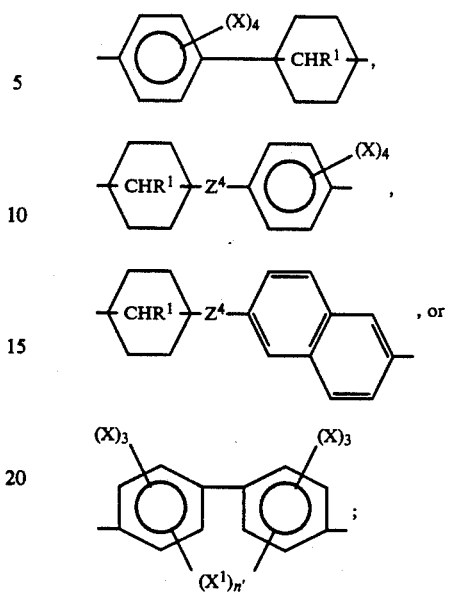

and $Z^4$ is —CO—O—, —O—CO—, —NR$^1$—CO— or —CO—NR$^1$—; $X^1$ is a divalent hydrocarbyl group having from 1 to about 10, preferably from 1 to about 4, carbon atoms which can contain one or more heteroatoms selected from N, O or S and may be saturated or unsaturated; each R and $R^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; and n' is zero or one; and (B) a curing amount of one or more polyamines containing one or more rodlike mesogenic moieties.

The term "mesogenic" as is used herein designates compounds containing one or more rigid rodlike structural units which have been found to favor the formation of liquid crystal phases in the case of low molar mass substances. Thus the mesogen or mesogenic moiety is that structure responsible for molecular ordering.

DETAILED DESCRIPTION OF THE INVENTION

The epoxide compositions suitable for use in the present invention can be prepared by reacting the corresponding hydroxyl containing compound with an epihalohydrin by any suitable means known to those skilled in the art. Suitable such methods are disclosed by Lee and Neville in *Handbook of Epoxy Resins*, McGraw-Hill, (1967) which is incorporated herein by reference in its entirety.

Generally, the hydroxyl containing compound is reacted with an epihalohydrin in the presence of a suitable catalyst and in the presence or absence of a suitable solvent at a temperature suitably from about 0° C. to about 100° C., more suitably from about 20° C. to about 80° C., most suitably from about 20° C. to about 65° C.; at pressure suitably from about 30 mm Hg vacuum to about 100 psia., more suitably from about 30 mm Hg vacuum to about 50 psia., most suitably from about atmospheric pressure to about 20 psia.; and for a time $Z^2$ is a group represented by a cyclic or bicyclic ring system containing from 5 to about 12 carbon atoms and may be cycloaliphatic, polycycloaliphatic, aromatic or a combination thereof; n is 0 to 2; each $Z'$ is independently a —CO—, —O—CO—, —CO—O—, —CO—NR$^1$—, or —NR$^1$—CO— group and each n' independently has a value of zero or one; or the following Formula II

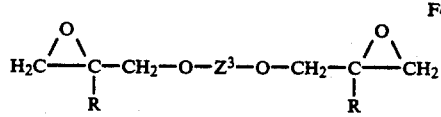

Formula II wherein $Z^3$ is sufficient to complete the reaction, usually from about 1 to about 12, more usually from about 1 to about 5, most usually from about 1 to about 3 hours. This initial reaction unless the catalyst is an alkali metal or alkaline earth metal hydroxide employed in stoichiometric quantities produces a halohydrin intermediate which is then reacted with a basic acting compound to convert the vicinal chlorohydrin groups to epoxide groups. The resultant product is a glycidyl ether compound.

Suitable epihalohydrins which can be employed to prepare the epoxide compounds include, for example, those represented by the following Formula XII

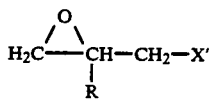
Formula XII wherein R is as previously defined; and X' is a halogen. Particularly suitable such epihalohydrins include, for example, epichlorohydrin, epibromohydrin, epiiodohydrin, methylepichlorohydrin, methylepibromohydrin, methylepiiodohydrin, combinations thereof and the like.

Suitable hydroxyl containing compounds which can be employed to prepare the epoxide compounds include, for example, those represented by the following Formulas XIII, XIV, XV or XVI

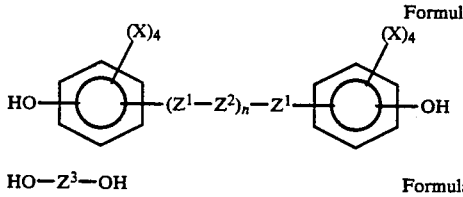
Formula XIII

HO—$Z^3$—OH          Formula XIV

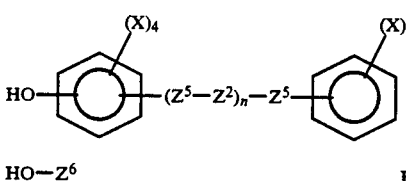
Formula XV

HO—$Z^6$          Formula XVI wherein at least about 80 percent of the -($Z^1$-$Z^2$)$_n$-$Z^1$- or -($Z^5$-$Z^2$)$_n$-$Z^5$- linkages and the hydroxyl groups are in the para position with respect to each other; n, $Z^1$, $Z^2$, $Z^3$, $Z^5$, $Z^6$ and X are as previously defined.

Particularly suitable hydroxyl containing compounds include, for example, 4,4'-dihydroxy-α-methylstilbene, 4,4'-dihydroxybenzanilide, 4,4'-dihydroxy-2,2'-dimethylazoxybenzene, 4,4'-dihydroxystilbene, 4,4'-dihydroxyazobenzene, 4,4'-dihydroxyazoxybenzene, 4,4'-dihydroxy-α-cyanostilbene, 4,4'-dihydroxydiphenylacetylene, N,N'-bis(4-hydroxyphenyl-terephthalamide, 4,4'-dihydroxy-3,3',5,5'-tetramethylstilbene, 4,4'-dihydroxy-3,3',5,5'-tetrabromostilbene, 4,4'-dihydroxy-3,3',5,5'-tetramethyl-α-methylstilbene, N-biphenyl-4-hydroxybenzamide, N-2-naphthyl-4-hydroxybenzamide, N-phenyl-4-hydroxybenzamide, N-(4'-hydroxyphenylbenzamide, 4-hydroxystilbene, 4-hydroxy-α-methylstilbene, 4-hydroxyazobenzene, 4-hydroxy-α-cyanostilbene, 4-hydroxyazoxybenzene, combinations thereof and the like.

Suitable catalysts which can be employed to prepare the epoxide compounds include, for example, ammonium halides such as, for example, benzyltrimethylammonium chloride, benzyltrimethylammonium bromide, tetrabutylammonium chloride, tetrabutylammonium bromide, tetraoctylammonium chloride, tetraoctylammonium bromide, tetramethylammonium chloride, tetramethylammonium bromide, combinations thereof and the like.

Suitable basic acting compounds which can be employed to prepare the epoxide compounds include, for example, alkali metal or alkaline earth metal hydroxides, carbonates, bicarbonates and the like. Particularly suitable such compounds include, for example, sodium hydroxide, potassium hydroxide, lithium hydroxide, calcium hydroxide, barium hydroxide, magnesium hydroxide, manganese hydroxide, sodium carbonate, potassium carbonate, lithium carbonate, calcium carbonate, barium carbonate, magnesium carbonate, manganese carbonate, sodium bicarbonate, potassium bicarbonate, lithium bicarbonate, calcium bicarbonate, barium bicarbonate, magnesium bicarbonate, manganese bicarbonate, mixtures thereof and the like. Most preferred is sodium hydroxide or potassium hydroxide.

Suitable solvents which can be employed herein include, for example, alcohols, aliphatic hydrocarbons, aromatic hydrocarbons, glycol ethers, amides, sulfoxides, sulfones, combinations thereof and the like. Particularly suitable solvents include, for example, methanol, ethanol, isopropanol, hexane, hetpane, octane, nonane, decane, toluene, xylene, ethylene glycol methyl ether, ethylene glycol ethyl ether, ethylene glycol n-butyl ether, ethylene glycol phenyl ether, propylene glycol methyl ether, propylene glycol phenyl ether, tripropylene glycol methyl ether, diethylene glycol methyl ether, diethylene glycol ethyl ether, diethylene glycol n-butyl ether, diethylene glycol phenyl ether, butylene glycol methyl ether, N,N-dimethylformamide, N-methylpyrrolidinone, N,N-dimethylacetamide, dimethylsulfoxide, sulfolane, combinations thereof and the like.

The solvent is usually employed in amounts suitably from about 5 to about 95, more suitably from about 20 to about 60, most suitably from about 30 to about 40, percent by weight based upon the combined weight of solvent and epihalohydrin.

Suitable compounds having an average of more than one active hydrogen atom per molecule which can be employed to prepare the advanced resins suitable for use in the present invention include, for example, bisphenols, thiobisphenols, dicarboxylic acids and compounds containing one primary amine or amide group or two secondary amine groups such as those represented by Formulas XVII or XVIII.

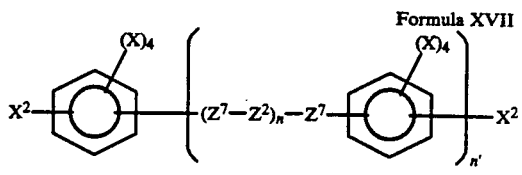
Formula XVII

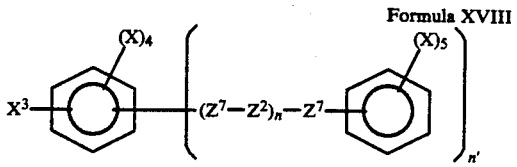
Formula XVIII wherein $X^2$ is independently a hydroxyl, carboxylic acid, —SH, or —$NHR^2$ group; $R^2$ is an alkyl group having from 1 to about 4 carbon atoms; $X^3$ is $NH_2$, $NH_2$—$SO_2$—, $NH_2$—CO—, or $NH_2$—$Z^8$—O—; $Z^8$ is an alkyl or cycloalkyl group having from 1 to about 12 carbon atoms; $Z^7$ can independently be a divalent hydrocarbyl group having from 1 to about 10, preferably from 1 to about 4 carbon atoms, —O—, —CO—, —SO—, —$SO_2$—, —S—, —S—S—, —$CR^1$=$CR^1$—, —$CR^1$=$CR^1$—$CR^1$=$CR^1$—, —$CR^1$=N—N=$CR^1$—, —$CR^1$=$CR^1$—CO—O—$CH_2$—, —$CR^1$=$CR^1$—CO—O—$CH_2$—$CH_2$—, —$CH_2$—O—CO—$CR^1$=$CR^1$—, —$CH_2$—$CH_2$—O—CO—$CR^1$=$CR^1$—, —$CR^1$=$CR^1$—CO—O—, —O—CO—$CR^1$=$CR^1$—, —N=N—, —CO—$NR^1$—, —$NR^1$—CO—, —CO—$NR^1$—$NR^1$—CO—, —C≡C—, —C≡C—C≡C—, —CO—S—, —S—CO—, —$CR^1$=N—, —N=$CR^1$, —CO—O—, —O—CO—, —$CR^1$=$CR^1$—CO—, —CO—$CR^1$=$CR^1$—, —$CR^1$=$CR^1$—O—CO—$CH_2$—, —$CH_2$—CO—O—$CR^1$=$CR^1$—, —$CR^1$=$CR^1$—O—CO—$CH_2$—$CH_2$—, —$CH_2$—$CH_2$—CO—O—$CR^1$=$CR^1$—, —$CH_2$—$CH_2$—CO—O—, —O—CO—$CH_2$—$CH_2$—, —CO—O$CR^1$=$CR^1$—, —$CR^1$=$CR^1$—O—CO—, a direct single bond,

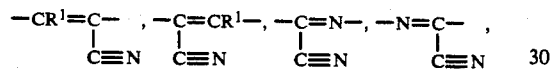

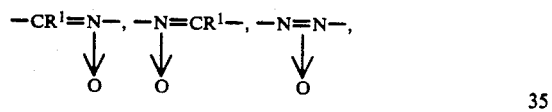

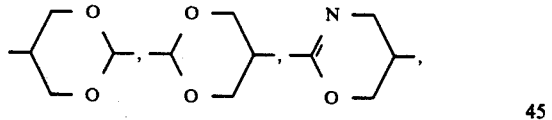

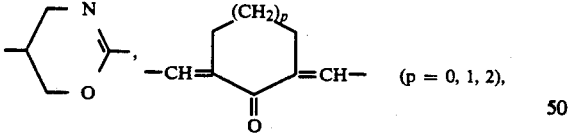

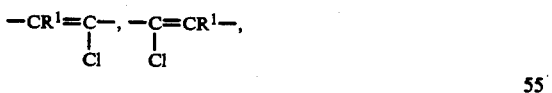

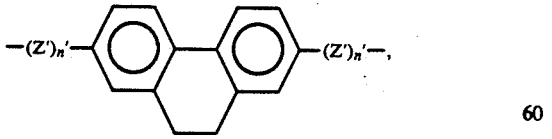

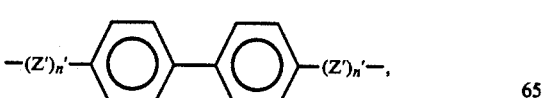

-continued

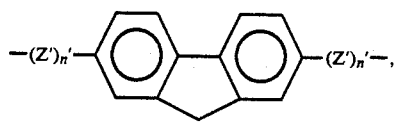

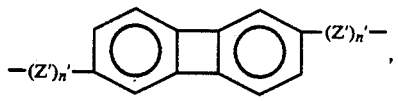

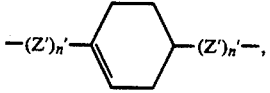

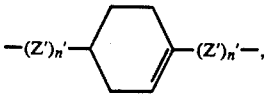

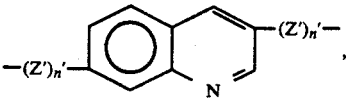

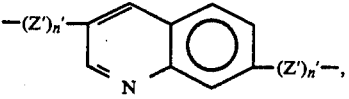

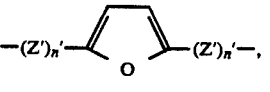

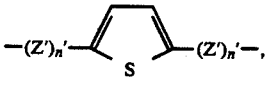

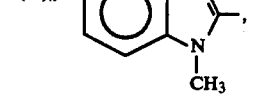

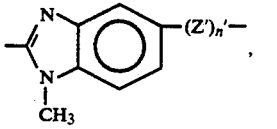

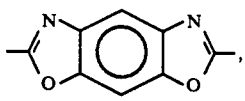

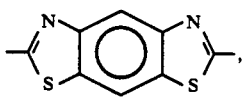

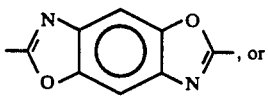, or

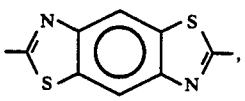

and wherein X, Z', $R^1$, $Z^2$, n and n' are as hereinbefore defined.

The advancement of the epoxy resins containing one or more rodlike mesogenic moieties with compounds having an average of more than one active hydrogen per molecule is employed to linearly chain extend the resin. This linear chain extension is required for some mesogenic-containing resin compositions in order to obtain liquid crystal character. The advancement of the rodlike mesogenic epoxy resins can also be used to increase the temperature range in which a particular resin is liquid crystalline and to control the degree of crosslinking during the final curing stage.

The epoxy resin containing one or more rodlike mesogenic moieties and the compound having an average of more than one active hydrogen atom per molecule are reacted in amounts which provide suitably from about 0.01:1 to about 0.95:1, more suitably from about 0.05:1 to about 0.9:1, most suitably from about 0.10:1 to about 0.50:1 active hydrogen atoms per epoxy group.

Particularly suitable compounds having an average of more than one active hydrogen atom per molecule which can be employed herein include hydroxy-containing compounds, carboxylic acid-containing compounds and primary amine-containing compounds. These compounds include, for example, those represented by Formulas XVII and XVIII.

Particularly suitable hydroxyl-containing compounds include, for example, hydroquinone, bisphenol A, 4,4'-dihydroxydiphenylmethane, 4,4'-thiodiphenol, 4,4'-sulfonyldiphenol, 4,4'-dihydroxydiphenyl oxide, 4,4'-dihydroxybenzophenone, 1,1-bis(4-hydroxyphenyl)-1-phenylethane, 3,3',5,5'-tetrachorobisphenol A, 3,3'-dimethoxybisphenol A, 4,4'-dihydroxybiphenyl, 4,4'-dihydroxy-α,α'-diethylstilbene, 4,4'-dihydroxy-α-methylstilbene, 4,4'-dihydroxybenzanilide, 4,4'-dihydroxy-2,2'-dimethylazoxybenzene, 4,4'-dihydroxy-α-cyanostilbene, bis(4-hydroxyphenyl)terephthalate, N,N'-bis(4-hydroxyphenyl)terephthalamide, bis(4'-hydroxybiphenyl)terephthalate, 4,4'-dihydroxyphenylbenzoate, bis(4'-hydroxyphenyl)-1,4-benzenediimine, 4,4''-dihydroxybiphenylbenzoate, 1,4-bis(4'-hydroxyphenyl-1'-carboxamide)benzene, 1,4-bis(4'-hydroxyphenyl-1'-carboxy)benzene, 4,4'-bis(4''-hydroxyphenyl-1''-carboxy)biphenyl, mixtures thereof and the like.

Particularly suitable carboxylic acid-containing compounds include, for example, terephthalic acid, 4,4'-benzanilide dicarboxylic acid, 4,4'-phenylbenzoate dicarboxylic acid, 4,4'-stilbenedicarboxylic acid and mixtures thereof and the like.

Particularly suitable primary amine-containing compounds include, for example, aniline, 4'-sulfonamido-N-phenyl benzamide, 4'-sulfonamido-N'-phenyl-4-chlorobenzamide, 4-amino-1-phenylbenzoate, 4-amino-N-phenylbenzamide, N-phenyl-4-aminophenyl-1-carboxamide, phenyl-4-aminobenzoate, biphenyl-4-aminobenzoate, 1-phenyl-4'-aminophenylterephthalate, mixtures thereof and the like.

The advancement reaction can be conducted in the presence of a suitable advancement catalyst such as, for example, phosphines, quaternary ammonium compounds, phosphonium compounds, tertiary amines and the like. Particularly suitable catalysts include, for example, ethyltriphenylphosphonium chloride, ethyltriphenylphosphonium bromide, ethyltriphenylphosphonium iodide, ethyltriphenylphosphonium diacetate (ethyltriphenylphosphonium acetate.acetic acid complex), ethyltriphenylphosphonium phosphate, tetrabutylphosphonium chloride, tetrabutylphosphonium bromide, tetrabutylphosphonium iodide, tetrabutylphosphonium diacetate (tetrabutylphosphonium acetate.acetic acid complex), butyltriphenylphosphonium tetrabromobisphenate, butyltriphenylphosphonium bisphenate, butyltriphenylphosphonium bicarbonate, benzyltrimethylammonium chloride, tetramethylammonium hydroxide, triethylamine, tripropylamine, tributylamine, 2-methylimidazole, benzyldimethylamine, mixtures thereof and the like. Many of these catalysts are described in U.S. Pat. Nos. 3,306,872; 3,341,580; 3,379,684; 3,477,990; 3,547,881; 3,637,590; 3,843,605; 3,948,855; 3,956,237; 4,048,141; 4,093,650; 4,131,633; 4,132,706; 4,171,420; 4,177,216 and 4,366,295, all of which are incorporated herein by reference.

The amount of advancement catalyst depends, of course, upon the particular reactants and catalyst employed; however, it is usually employed in quantities of from about 0.03 to about 3, preferably from about 0.03 to about 1.5, most preferably from about 0.05 to about 1.5 percent by weight based upon the weight of the epoxy-containing compound.

The advancement reaction can be conducted at atmospheric, superatmospheric or subatmospheric pressures at temperatures of from about 20° C. to about 260° C., preferably from about 80° C. to about 240° C., more preferably from about 100° C. to about 200° C. The time required to complete the advancement reaction depends upon the temperature employed. Higher temperatures require shorter periods of time whereas lower temperatures require longer periods of time. Generally, however, times of from about 5 minutes to about 24 hours, preferably from about 30 minutes to about 8 hours, more preferably from about 30 minutes to about 3 hours are suitable.

If desired, the advancement reaction can be conducted in the presence of one or more solvents. Suitable such solvents include, for example, glycol ethers, aliphatic and aromatic hydrocarbons, aliphatic ethers, cyclic ethers, ketones, esters, amides, combinations thereof and the like. Particularly suitable solvents include, for example, toluene, benzene, xylene, methyl ethyl ketone, methyl isobutyl ketone, diethylene glycol methyl ether, dipropylene glycol methyl ether, dimethylformamide, dimethylsulfoxide, N-methylpyrrolidinone, tetrahydrofuran, propylene glycol methyl ether, combinations thereof and the like. The solvents can be employed in amounts of from about zero to about 80%, preferably from about 20% to about 60%, more preferably from about 30% to about 50% by weight based upon the weight of the reaction mixture.

The mesogenic polyamines employed in the present invention include any polyamine containing at least one rodlike mesogenic moiety and an average of two or more amine hydrogens reactive with an epoxide group per molecule. Suitable such polyamines which can be employed to prepare the curable and cured compositions of the present invention include, for example, those represented by either the following Formula XIX,

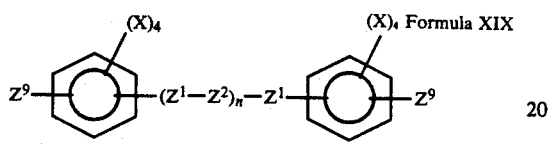

wherein at least about 80 percent of the $-(Z^1-Z^2)_n-Z^1-$ linkages and the $Z^9$ groups are in the para position with respect to each other; each $R^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), $-NO_2$, or $-C\equiv N$; each $Z^1$ is independently $-CR^1=CR^1-$, $-CR^1=CR^1-CR^1=CR^1-$, $-CR^1=N-N=CR^1-$, $-CR^1=CR^1-CO-O-CH_2-$, $-CR^1=CR^1-CO-O-CH_2-CH_2-$, $-CH_2-O-CO-CR^1=CR^1-$, $-CH_2-CH_2-O-CO-CR^1=CR^1-$, $-CR^1=CR^1-CO-O-$, $-O-CO-CR^1=CR^1-$, $-CO-NR^1-$, $-NR^1-CO-$, $-CO-NR^1-NR^1-CO-$, $-C\equiv C-$, $-C\equiv C-C\equiv C-$, $-N=N-$, $-CO-S-$, $-S-CO-$, $-CR^1=N-$, $-N=CR^1-$, $-CO-CR^1=CR^1-$, $-CR^1=CR^1-CO-$, $-CR^1=CR^1-O-CO-CH_2-$, $-CH_2-CO-O-CR^1=CR^1-$, $-CR^1=CR^1-O-CO-CH_2-CH_2-$, $-CH_2-CH_2-CO-O-CR^1=CR^1-$, $-CH_2-CH_2-CO-O-$, $-O-CO-CH_2-CH_2-$, $-CO-O-CR^1=CR^1-$, $-CR^1=CR^1-O-CO-$,

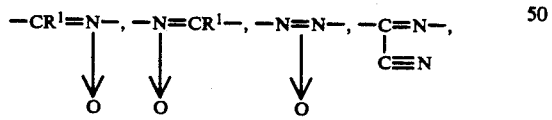

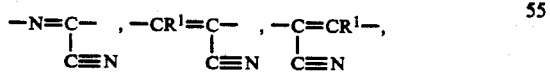

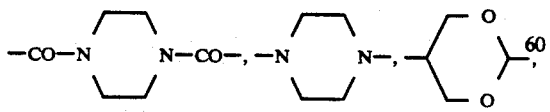

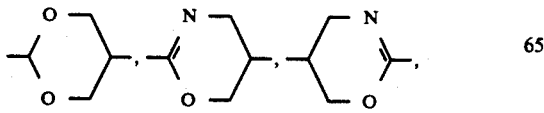

-continued

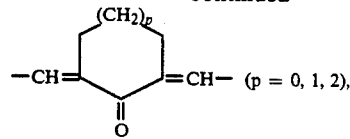
$-CH=\overset{(CH_2)_p}{\underset{O}{\bigcirc}}=CH-$ (p = 0, 1, 2),

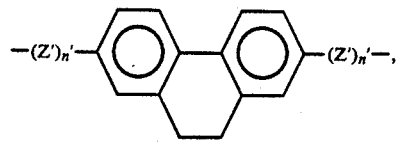
$-(Z')_{n'}-\phantom{X}-(Z')_{n'}-$,

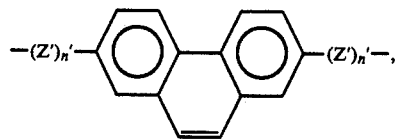
$-(Z')_{n'}-\phantom{X}-(Z')_{n'}-$,

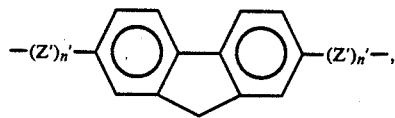
$-(Z')_{n'}-\phantom{X}-(Z')_{n'}-$,

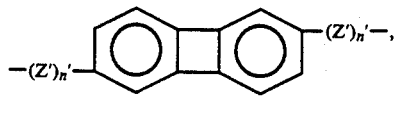
$-(Z')_{n'}-\phantom{X}-(Z')_{n'}-$,

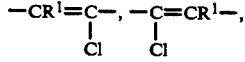
$-CR^1=\underset{Cl}{C}-$, $-\underset{Cl}{C}=CR^1-$,

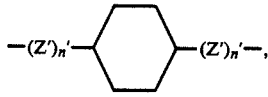
$-(Z')_{n'}-\phantom{X}-(Z')_{n'}-$,

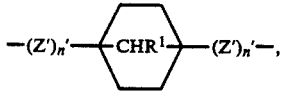
$-(Z')_{n'}-CHR^1-(Z')_{n'}-$,

$-(Z')_{n'}-\phantom{X}-(Z')_{n'}-$,

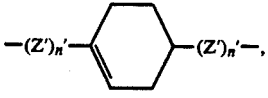
$-(Z')_{n'}-\phantom{X}-(Z')_{n'}-$,

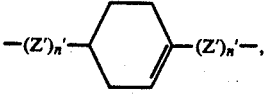
$-(Z')_{n'}-\phantom{X}-(Z')_{n'}-$,

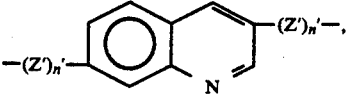
$-(Z')_{n'}-\phantom{X}-(Z')_{n'}-$,

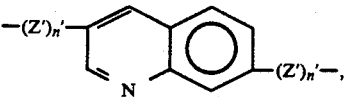
$-(Z')_{n'}-\phantom{X}-(Z')_{n'}-$,

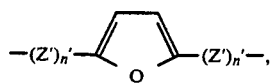

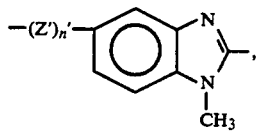

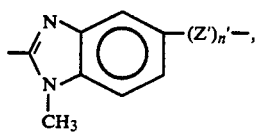

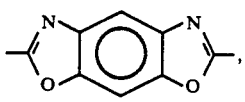

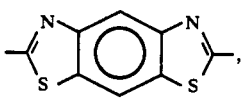

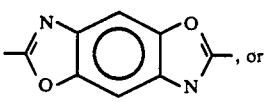

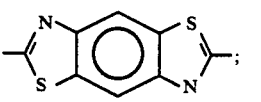

$Z^2$ is a group represented by a cyclic or bicyclic ring system containing from 5 to about 12 carbon atoms and may be cycloaliphatic, polycycloaliphatic, aromatic or a combination thereof; n is 0 to 2; each $Z^9$ is independently a —NHR$^1$, —O—(CHR$^1$)$_n$—CHR$^1$—NHR$^1$, —NR$^1$—(CHR$^1$)$_n$—CHR$^1$—NHR$^1$,

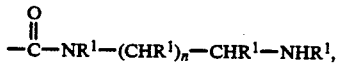

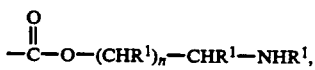

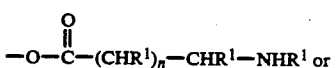

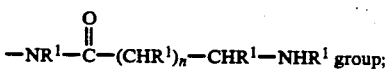

each Z' is independently a —CO—, —O—CO—, —CO—O—, —CO—NR$^1$—, or —NR$^1$—CO— group and each n' independently has a value of zero or one; or the following Formula XX $Z^9$—$Z^3$—$Z^9$          Formula XX wherein $Z^3$ is

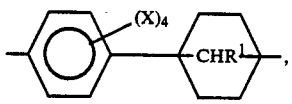

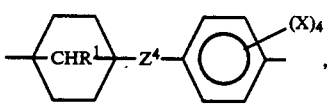

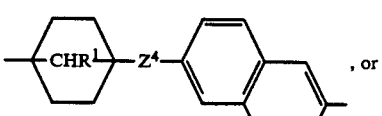

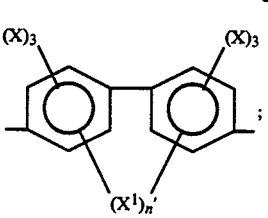

and $Z^4$ is —CO—O—, —O—CO—, —NR$^1$—CO— or —CO—NR$^1$—; $X^1$ is a divalent hydrocarbyl group having from 1 to about 10, preferably from 1 to about 4, carbon atoms which can contain one or more heteroatoms selected from N, O or S and may be saturated or unsaturated; each R$^1$ is independently hydrogen or an aliphatic hydrocarbon group having from 1 to about 4 carbon atoms; each X is independently hydrogen, a hydrocarbyl or hydrocarbyloxy group having suitably from 1 to about 12, more suitably from 1 to about 6, most suitably from 1 to about 4, carbon atoms, a halogen atom (preferably chlorine or bromine), —NO$_2$, or —C≡N; and n' is zero or one; and $Z^9$ is as hereinbefore defined.

The curable compositions of the present invention can additionally contain one or more of any suitable curing agents for curing epoxy resins such as, for example, primary and secondary polyamines, carboxylic acids and anhydrides thereof, aromatic hydroxyl containing compounds, imidazoles, guanidines, urea-aldehyde resins, melamine-aldehydes resins, alkoxylated urea-aldehyde resins, alkoxylated melamine-aldehyde resins, aliphatic amines, cycloaliphatic amines, aromatic amines, combinations thereof and the like. Particularly suitable curing agents include, for example, methylene dianiline, dicyandiamide, ethylene diamine, diethylenetriamine, triethylenetetramine, tetraethylenepentamine, urea-formaldehyde resins, melamine-formaldehyde resins, methylolated urea-formaldehyde resins, methylolated melamine-formaldehyde resins, phenol-formaldehyde novolac resins, cresol-formaldehyde novolac resins, sulfanilamide, diaminodiphenylsulfone, diethyltoluenediamine, t-butyltoluenediamine, bis-4-aminocyclohexylmethane, isophoronediamine, diaminocyclohexane, hexamethylenediamine, piperazine, aminoethylpiperazine, 2,5-dimethyl-2,5-hexanediamine, 1,12-dodecanediamine, tris-3-aminopropylamine, combinations thereof and the like.

The polyamines containing one or more rodlike mesogenic moieties are employed in the present invention in amounts which will effectively cure the composition; however, these amounts will depend upon the particular epoxy resin and polyamine employed. Generally, suitable amounts include, for example, from about 0.95:1 to about 1.2:1 amine hydrogen equivalents of polyamine per epoxide equivalent of epoxy resin.

The monoepoxide compounds containing one or more rodlike mesogenic moieties which may be employed in the present invention can serve as reactive diluents for the curable compositions of the present invention. Said monoepoxide compounds also provide a means of incorporating into the composition, additional or structurally different rodlike mesogenic moieties so as to enhance or modify properties when cured.

Epoxy resins free of rodlike mesogenic moieties which may be employed in the curable compositions of the present invention include, for example, the diglycidyl ethers of resorcinol, bisphenol A, 4,4'-dihydroxydiphenylmethane, 3,3',5,5'-tetrabromobisphenol A, 4,4'-thiodiphenol, 4,4'-sulfonyldiphenol, 4,4'-dihydroxydiphenyl oxide, 4,4'-dihydroxybenzophenone, 1,1-bis(4-hydroxyphenyl)-1-phenylethane, 3,3', 5,5'-tetrachlorobisphenol A, 3,3'-dimethoxybisphenol A; the triglycidyl ether of tris(hydroxyphenyl)methane; the polyglycidyl ether of a phenol or substituted phenolaldehyde condensation product (novolac); the polyglycidyl ether of a dicyclopentadiene or an oligomer thereof and phenol condensation product; the advancement reaction products of the aforesaid di- and polyglycidyl ethers with aromatic di- or polyhydroxyl- or carboxylic acid- containing compounds including, for example, bisphenol A (4,4'-isopropylidenediphenol), o-, m-, p-dihydroxybenzene, 2,4-dimethylresorcinol, 4-chlororesorcinol, tetramethylhydroquinone, 1,1-bis(4-hydroxyphenyl)ethane, 1,1-bis(4-hydroxyphenyl-1-phenylethane, 4,4'-dihydroxydiphenyl ether, 3,3', 5,5'-tetramethyldihydroxydiphenyl ether, 3,3',5,5'-dichlorodihydroxydiphenyl ether, 4,4'-bis(p-hydroxyphenyl isopropyl)diphenyl ether, 4,4'-bis(p-hydroxyphenoxy)benzene, 4,4'-bis(p-hydroxyphenoxy)diphenyl ether, 4,4'-bis(4-hydroxyphenoxy)phenyl sulfone)-diphenyl ether, 4,4'-dihydroxydiphenyl sulfone, 4,4'-dihydroxydiphenyl sulfide, 4,4'-dihydroxydiphenyl disulfide, 2,2'-dihydroxydiphenyl sulfone, 4,4'-dihydroxydiphenyl methane, 1,1-bis(p-hydroxyphenyl)cyclohexane, 4,4'-dihydroxybenzophenone, phloroglucinol, pyrogallol, 2,2',5,5'-tetrahydroxydiphenyl sulfone, tris(hydroxyphenyl)methane, dicyclopentadiene diphenol, tricyclopentadiene diphenol; mixtures thereof and the like.

Before and/or during processing and/or curing of the curable compositions into a part, electric or magnetic fields or shear stresses can be applied for the purpose of orienting the liquid crystal moieties contained or developed therein which in effect improves the mechanical properties. As specific examples of these methods, Finkelmann, et al, *Macromol. Chem.*, 180, 803-806 (March 1979) induced orientation in thermotropic methacrylate copolymers containing mesogenic side chain groups decoupled from the main chain via flexible spacers in an electric field. Orientation of mesogenic side chain groups decoupled from the polymer main chain via flexible spacers in a magnetic field has been demonstrated by Roth and Kruecke, *Macromol. Chem.*, 187, 2655-2662 (November 1986). Magnetic field induced orientation of mesogenic main chain containing polymers has been demonstrated by Moore, et al, *ACS Polymeric Material Sciences and Engineering*, 52, 84-86 (April-May 1985). Magnetic and electric field orientation of low molecular weight mesogenic compounds is discussed by W. R. Krigbaum in *Polymer Liquid Crystals*, pages 275-309 (1982) published by Academic Press, Inc. All of the above are incorporated herein by reference in their entirety.

In addition to orientation by electric or magnetic fields, polymeric mesophases can be oriented by shear forces which are induced by drawing and/or shear flow through dies, orefices, and mold gates. A general discussion for orientation of thermotropic liquid crystal polymers by this method is given by S. K. Garg and S. Kenig in *High Modulus Polymers*, pages 71-103 (1988) published by Marcel Dekker, Inc. For the mesomorphic systems based on the epoxy resin compositions, this shear orientation can be produced by processing methods such as injection molding, extrusion, pultrusion, filament winding, filming and prepreging.

The curable compositions of the present invention can be blended with other materials such as solvents or diluents, fillers, pigments, dyes, flow modifiers, thickeners, reinforcing agents, mold release agents, wetting agents, stabilizers, fire retardant agents, surfactants, combinations thereof and the like.

These additives are added in functionally equivalent amounts, e.g., the pigments and/or dyes are added in quantities which will provide the composition with the desired color; however, they are suitably employed in amounts of from about zero to about 20, more suitably from about 0.5 to about 5, most suitably from about 0.5 to about 3 percent by weight based upon the weight of the total blended composition.

Solvents or diluents which can be employed herein include, for example, hydrocarbons, ketones, glycol ethers,, aliphatic ethers, cyclic ethers, esters, amides, combinations thereof and the like. Particularly suitable solvents or diluents include, for example, toluene, benzene, xylene, methyl ethyl ketone, methyl isobutyl ketone, diethylene glycol methyl ether, dipropylene glycol methyl ether, dimethylformamide, N-methylpyrrolidinone, tetrahydrofuran, propylene glycol methyl ether, combinations thereof and the like.

The modifiers such as thickeners, flow modifiers and the like can be suitably employed in amounts of from zero to about 10, more suitable from about 0.5 to about 6, most suitably from about 0.5 to about 4 percent by weight based upon the weight of the total composition.

Reinforcing materials which can be employed herein include natural and synthetic fibers in the form of woven fabric, mats, monofilament, multifilament, unidirectional fibers, rovings, random fibers or filaments, inorganic fillers or whiskers, hollow spheres, and the like. Suitable reinforcing materials include, glass, ceramics, nylon, rayon, cotton, aramid, graphite, polyalkylene terephthalates, polyethylene, polypropylene, polyesters, combinations thereof and the like.

Suitable fillers which can be employed herein include, for example, inorganic oxides, ceramic microspheres, plastic microspheres, glass microspheres, inorganic whiskers, $CaCO_3$, combinations thereof and the like.

The fillers can be employed in amounts suitably from about zero to about 95, more suitably from about 10 to about 80, most suitable from about 40 to about 60 percent by weight based upon the weight of the total composition.

The following examples are illustrative of the present invention, but are not to be construed as to limiting its scope in any manner.

EXAMPLE 1

A. Synthesis of 4,4'-Dinitrostilbene

Nitrobenzyl chloride (126.97 grams, 0.74 mole), ethanol (1000 milliliters) and acetone (42.98 grams, 0.74 mole) are added to a reactor and stirred under a nitrogen atmosphere with cooling to provide a 15° C. mixture. Dropwise addition of a solution of sodium hydroxide (32.56 grams, 0.814 mole) in ethanol (600 milliliters) commences and is completed over the next 24 minutes inducing a reaction temperature increase to 23° C. After an additional seven minutes, the reaction temperature increases to 30° C. At this time heating commences and a reaction temperature of 76° C. at reflux is achieved 58 minutes later. After an additional 344 minutes of refluxing, the reactor contents are added to deionized water (one gallon) followed by acidification of the product slurry with hydrochloric acid to a pH of 2 with mixing. The resultant precipitated product is recovered by filtration. The wet filter cake is added to dimethylsulfoxide (950 milliliters) and heated to 140° C. to provide a solution. Recrystallization is accomplished by holding the dimethylsulfoxide solution at 5° C. overnight followed by filtration to recover the crystalline precipitate. A second recrystallization is accomplished by adding the wet filter cake to acetone (350 milliliters) followed by heating to a boil. Recrystallization is accomplished by holding the acetone solution at 5° C. overnight followed by filtration to recover the crystalline precipitate. The recovered filter cake is dried in a vacuum oven at 110° C. and 5 mm Hg to a constant weight of 63.2 grams. The product is light orange in color with a sparkling, metallic appearance. Additional solids precipitates from the dimethylsulfoxide mother liquor from the initial recrystallization, but not attempt is made to recover and process this material. Fourier transform infrared spectrophotometric analysis of a nujol mull of the product on a sodium chloride plate confirms the product structure (1503 and 1337 cm$^{-1}$ absorbances observed for the conjugated nitro group). Proton nuclear magnetic resonance spectroscopy further confirms the product structure. Differential scanning calorimetry of a portion (3.58 milligrams) of the product under a stream of nitrogen flowing at 35 cubic centimeters per minute and using a heating rate of 10° C. per minute with a range of 200° C. to 450° C. reveals a sharp melting point endotherm at 296° C. (enthalpy=88.39 J/g) followed by exothermic decomposition with a maximum peak value of 371° C. (enthalpy=613.17 J/g).

B. Synthesis of 4,4'-Diaminostilbene Dihydrochloride

A portion (40.5 grams, 0.15 mole) of 4,4'-dinitrostilbene from A above, concentrated hydrochloric acid (250 milliliters) and methanol (200 millileters) are added to a flask and maintained therein as stirred mixture. Over the next three hour period, 325 mesh powdered iron is added to the reaction mixture in one grams aliquots until a total of 22.0 grams (0.40 mole) has been added. With each added aliquot of iron, heating with vigorous hydrogen evolution occurs causing frothing of the reaction mixture. Frothing is moderated as needed by cooling of the flask on a sodium chloride and ice bath between iron additions. After completion of the iron addition, the mixture is heated for 16 hours at reflux then cooled to room temperature (25° C.) and filtered. The dark brown liquid filtrate is concentrated by rotary evaporation under vacuum at 85° C. to one half original volume then decolorized by the addition of activated charcoal. After filtration, the filtrate is desalted by passing through a column of Sephadex G-50. The eluate is rotary evaporated under vacuum to provide a pale tan colored solid. Recovery of this solid followed by drying in a vacuum oven at 110° C. and 5 mm Hg provides a constant product weight of 29.4 grams. Fourier transform infrared spectrophotometric analysis of a nujol mull of the product on a sodium chloride plate confirms the product structure (disappearance of the absorbances observed for the conjugated nitro group, appearance of —NH$_3$+ stretching absorbances at 3040, 2603 and 2550 cm$^{-1}$ and appearance of a —NH$_3$+ bending absorbance at 1497 cm$^{-1}$). Proton nuclear magnetic resonance spectroscopy further confirms the product structure. Differential scanning calorimetry of a portion (3.62 milligrams) of the product under a stream of nitrogen flowing at 35 cubic centimeters per minute and using a heating rate of 10° C. per minute with a range of 200° C. to 450° C. reveals a endotherm at 263° C. (enthalpy=162.85 J/g) followed by second endotherm at 291° C. (enthalpy=337.82 J/g).

C. Dehydrochlorination of 4,4'-Diaminostilbene Dihydrochloride

A portion (29.10 grams, 0.2055 hydrochloride equivalents) of 4,4'-diaminostilbene dihydrochloride from B above and dry ethanol (500 grams) are added to a reactor and stirred under a nitrogen atmosphere with heating to 70° C. Once the 70° C. temperature is achieved, an initial aliquot of triethylamine (20.79 grams, 0.2055 mole) is added to the slurry over a one minute period causing immediate clearing to a solution accompanied by an exotherm to 72° C. After an additional 29 minutes at 70° C., a second aliquot of triethylamine (20.79 grams, (0.2055 mole) is added to the solution. After an additional 30 minutes at the 70° C. temperature, the reactor contents are recovered and rotary evaporated under vacuum to provide a light tan colored powder product. The product is washed with four 500 milliliter portions of deionized water with filtration completed between each washing to recover the product. The filter cake recovered from the final wash is dried in a vacuum oven at 100° C. and 2 mm Hg to a constant product weight of 20.60 grams of light tan colored 4,4'-diaminostilbene powder.

EXAMPLE 2

A. Synthesis of 4,4'-Dinitrobenzanilide

4-Nitrobenzoyl chloride (111.34 grams, 0.60 mole), triethylamine (72.86 grams, 0.72 mole), 4-(N,N'-dimethylamino)pyridine (1.94 grams, 1.0% wt. of the 4-nitrobenzoyl chloride and 4-nitroaniline used) and tetrahydrofuran (250 milliliters) are added to a reactor and stirred under a nitrogen atmosphere with cooling to provide a 5° C. solution. Dropwise addition of a solution of 4-nitroaniline (82.88 grams, 0.60 mole) in tetrahydrofuran (400 milliliters) commenced and is completed over the next 30 minutes while maintaining a reaction temperature of 5° C. to 8° C. After completion of addition of the 4-nitroaniline and tetrahydrofuran solution the reaction temperature is allowed to increase to room temperature (24° C.) over a 106 minute period. After the reaction is held at room temperature for two hours, the reactor contents are added to deionized water (1.5 gallons). The resultant precipitated product is recovered by filtration then washed with deionized water (500 milliliters). The wet filter cake is added to acetone (500 milliliters) and heated to boiling with stirring. The acetone suspension is held at 2° C. overnight followed by filtration to recover the crystalline precipitate. The recovered filter cake is dried in a vacuum oven at 110° C. and 5 mm Hg to a constant weight of 84.7 grams. The product is light yellow in color with a brilliant appearance. Additional solids precipitated from the acetone mother liquor from the initial filtration upon concentration by rotary evaporation, but no attempt is made to recover and process this material. Fourier transform infrared spectrophotometric analysis of a nujol mull of the product on a sodium chloride plate confirms the product structure (1538 and 1336 cm$^{-1}$ absorbances observed for the conjugated nitro group, secondary amide N—H stretching (solid state) absorbance observed at 3368 cm$^{-1}$, and secondary amide carbonyl stretching (solid state) absorbance observed at 1686 cm$^{-1}$). Proton nuclear magnetic resonance spectroscopy further confirms the product structure.

B. Synthesis of 4,4'-Diaminobenzanilide

A portion (22.0 grams, 0.1532 nitro equivalents) of 4,4'-dinitrobenzanilide from A above and ethanol (300 milliliters) are added to a 400 milliliter heavy walled glass bottle and then sparged with nitrogen. After removal of air by nitrogen sparging, Raney nickel catalyst (6.0 grams of a 75% wt. slurry in water at pH 10) is added to the slurry in the glass bottle which is then stoppered and multiply purged with hydrogen to replace the nitrogen atmosphere. The bottle is then placed on a shaking type agitator, and pressurized to 46.5 psig hydrogen. Shaking of the pressurized slurry at room temperature (25° C.) commences until 20.7 hours later, the hydrogen pressure reading indicated that 42 psig of hydrogen has been consumed. The product slurry is recovered, diluted into dimethylsulfoxide (250 milliliters) to provide a solution of product containing precipitated Raney nickel, then filtered through a medium porosity fritted glass funnel. The recovered dimethylsulfoxide product solution is rotary evaporated at 130° C. under vacuum to provide a solid product. The solid product is further dried in a vacuum oven at 120° C. and 3 mm Hg to a constant weight of 16.98 grams. The product thus recovered is light golden orange in color. Fourier transform infrared spectrophotometric analysis of a nujol mull of the product on a sodium chloride plate confirms the product structure (disappearance of the absorbances observed for the conjugated nitro group, secondary amide N—H stretching (solid state) and primary amine N—H group stretching absorbances observed at 3393, 3318 and 3207 cm$^{-1}$ and secondary amide carbonyl stretching (solid state) absorbance observed at 1630 cm$^{-1}$). Proton magnetic resonance spectroscopy further confirms the product structure.

EXAMPLE 3

A. Synthesis of 4,4'-Dihydroxy-alpha-methylstilbene

Phenol (188.22 grams, 2.0 moles) and chloroacetone (102.81 grams, 1.0 mole as chloroacetone) are added to a reactor and cooled to −10° C. with stirring. The chloroacetone used is a technical grade containing 90% chloroacetone, 2.5% acetone, 6.5% 1,1-dichloroacetone and 1.0% 1,3-dichloroacetone. Concentrated sulfuric acid (98.08 grams, 1.0 mole) is added dropwise to the stirred solution over a one hour period in order to maintain the reaction temperature between −10° C. and −11° C. After two hours of post reaction at the −10° C. temperature, the viscous orange oil product is mixed with 500 milliliters of iced deionized water. The oil product is separated then washed with a second 500 milliliter portion of chilled deionized water. After separation, the recovered oil product is added to a 2-liter beaker along with 250 milliliters of ethanol and stirred to provide a solution. Deionized water (250 milliliters) is added to the stirred solution and heating commenced. As the temperature of the mixture increases, the stirred mixture begins to clear. Each time clearing is observed, sufficient deionized water is added to induce cloudiness, followed by continuation of the mixing and heating. Once the temperature reaches 90° C., a massive precipitation of white crystalline plates occurs. At this time, heating and stirring ceases and the mixture is chilled to 5° C. and held therein for 12 hours. The crystalline produce is recovered by filtration, washed with two 150 milliliter portions of deionized water, then dried at 90° C. and 5 mm Hg to a constant weight of 103 grams. Nuclear magnetic resonance spectroscopy and infrared spectrophotometric analysis confirms the product structure for 4,4'-dihydroxy-α-methylstilbene.

B. Epoxidation of 4,4'-Dihydroxy-α-methylstilbene 4,4'-dihydroxy-α-methylstilbene (113.13 grams, 1.0 hydroxyl equivalent) prepared using the method of A above, epichlorohydrin (462.65 grams, 5 moles), deionized water (40.23 grams, 8.0 percent by weight of the epichlorohydrin used) and isopropanol (249.12 grams, 35 percent by weight of the epichlorohydrin used) are added to a reactor and heated to 55° C. with stirring under a nitrogen atmosphere. Once the 55° C. reaction temperature is achieved, sodium hydroxide (36.0 grams, 0.90 mole) dissolved in deionized water (144 grams) is added dropwise to the reactor over a 40 minute period in order to maintain a reaction temperature between 55° and 59° C. Ten minutes after completion of the aqueous sodium hydroxide addition, the stirring is stopped and the aqueous layer which separates from the reaction mixture is pipetted off and discarded. Stirring is resumed and after a total of twenty minutes following completion of the initial aqueous sodium hydroxide addition, a second solution of sodium hydroxide (16.0 grams, 0.40 mole) dissolved in deionized water (64 grams) is added to the reactor over a twenty minute period so as to maintain the 55° C. reaction temperature. Fifteen minutes after completion of the aqueous sodium hydroxide addition, the recovered reaction mixture is added to a separatory funnel and washed with 750 milliliters of deionized water. The separated organic layer is washed a second time (750 milliliters deionized water), recovered and then rotary evaporated under vacuum for 45 minutes at 110° C. then 30 minutes at 130° C. The product is recovered (166.5 grams) as a crystalline off-white solid with an epoxide equivalent weight of 176.8.

C. Characterization of Liquid Crystallinity in the Diglycidyl Ether of 4,4'-Dihydroxy-α-methylstilbene A portion (23.5 milligrams) of the diglycidyl ether of 4,4'-dihydroxy-alpha-methylstilbene from B above is analyzed by differential scanning calorimetry using a heating rate of 5° C. per minute and a temperature range of 30° C. to 145° C. The results are reported in Table I.

TABLE I

DIFFERENTIAL SCANNING CALORIMETRY ANALYSIS OF THE DIGLYCIDYL ETHER OF 4,4'-DIHYDROXY-α-METHYLSTILBENE

| Cycle Designation | Observed Transition Temperatures (°C.) midpoint/range | Enthalpy (J/g) | Comments |
|---|---|---|---|
| First heat (30 to 145° C.) | 128/100–135 | 75.0 | endotherm |
| First cooling (145 to 30° C.) | 84/85–75 | 1.37 | exotherm, onset to crystallization observed at 54° C. |
| Second heat (30 to 145° C.) | 67/55–85 | 12.6 | exotherm |
| | 126/105–137 | 62.7 | endotherm |
| Second cooling (145 to 30° C.) | 84/88–76 | 1.18 | exotherm, onset to crystallization observed at 47° C. |

Analysis of the diglycidyl ether via polarized light microscopy is completed using a microscope equipped with a programmable hot stage using a heating rate of 10° C. per minute. The results are reported in Table II.

TABLE II

POLARIZED LIGHT MICROSCOPY ANALYSIS OF THE DIGLYCIDYL ETHER OF 4,4'-DIHYDROXY-α-METHYLSTILBENE

| Cycle Designation | Observed Transition Temperatures (°C.) | Comments |
|---|---|---|
| First heat | 112 | First fluidity noted. |
| | 131 | Isotropization completed. |
| First cooling | 85 | First mobile nematic droplets observed. |
| | 62 | First crystallization noted. |

The diglycidyl ether is a monotropic liquid crystal with a nematic texture.

EXAMPLE 4

A. Synthesis of 4,4'-Dihydroxybenzanilide

One hundred grams of 4,4'-dihydroxybenzophenone (0.467 mole) is added to 300 milliliters of ethanol in a stirred, 1-liter Erlenmeyer flask. After the 4,4'-dihydroxybenzophenone has dissolved, a solution consisting of 48.6 grams of hydroxylamine hydrochloride (0.699 mole) and 57.4 grams of sodium acetate (0.700 mole) in 70 milliliters of deionized water is added followed by an additional 100 milliliters of ethanol. This mixture is stirred and heated on a hot plate to a gentle refluxing condition (75° C.). After heating for 4 hours, the solution is allowed to cool to room temperature with stirring and then filtered. One hundred milliliters of ethanol is used to wash the filter cake. The total filtrant obtained (600.4 grams) is then concentrated to a weight of 219.2 grams by evaporation of the ethanol and water. This solution is then placed in a stirred 1-liter Erlenmeyer flask to which 600 milliliters of deionized water is added. With the addition of the deionized water, a white precipitate is formed. After 30 minutes of stirring, this solution is filtered. The solids obtained weigh 98.22 grams after drying. Sixty-six grams of this material (4,4'-dihydroxybenzophenone oxime, 0.288 mole) is added to 330 milliliters of glacial acetic acid in a 500 milliliter round bottom flask equipped with a stirrer, water cooled condensor, nitrogen purge and heating mantle. A catalytic amount of toluenesulfonic acid (1.85 grams, 0.027 mole) is next added and the reaction mixture is then heated to 83° C. After heating for approximately 2 hours, a precipitate is formed which is stirred for an additional 2 hours at 87° C. Twenty-five milliliters of deionized water is next added and after 30 minutes, the contents of the reaction flask are transferred to a stirred, 1-liter Erlenmeyer flask. Immediately following this transfer, 400 milliliters of deionized water is added. This solution is stirred for 45 minutes and then filtered. The filter cake obtained is washed with 800 milliliters of deionized water and then dried. The resultant solids, which are a light beige color, weigh 54.82 grams. Fourier transform infrared analysis of this product shows absorbances which are indicative of the structure for 4,4'-dihydroxybenzanilide. Differential scanning calorimetry analysis shows a sharp melt endotherm at 273° C. for the 4,4'-dihydroxybenzanilide thus obtained.

B. Epoxidation of 4,4'-Dihydroxybenzanilide 4,4'-dihydroxybenzanilide (99.6 grams, 0.434 mole) prepared from the method given in A, epichlorohydrin (804.57 grams, 8.70 moles), deionized water (69.96 grams, 8.0 percent by weight of the epichlorohydrin used) and isopropanol (433.23 grams, 35 percent by weight of the epichlorohydrin used) are added to a round bottom flask and heated to 65° C. with stirring under a nitrogen atmosphere. After the temperature has reached 65° C., sodium hydroxide (31.31 grams, 0.78 mole) dissolved in deionized water (125.25 grams) is added dropwise over a one hour period so as to maintain the reaction temperature at 65° C. Fifteen minutes after completion of the aqueous sodium hydroxide addition, the stirring is stopped and the aqueous layer which separated from the reaction mixture is removed and discarded. Stirring is then resumed and a second solution of sodium hydroxide (13.92 grams, 0.35 mole) dissolved in deionized water (55.66 grams) is added over a 30 minute period so as to maintain the reaction temperature at 65° C. Fifteen minutes after completion of the second aqueous sodium hydroxide addition, stirring and heating are stopped and the reaction mixture is transferred to a separatory funnel. The aqueous layer which separated from the reaction mixture is removed and discarded. As the remaining organic layer cools to room temperature, sufficient methylene chloride is added to keep the epoxy resin dissolved in solution. The cooled organic layer obtained is then washed four times with deionized water. The volume of deionized water used during each wash is approximately one half that of the organic layer. The washed organic layer is then rotary evaporated under vacuum at 125° C. The final product obtained after drying is an off-white crystalline solid (142.03 grams, yield=95.8% based on 4,4'-dihydroxybenzanilide) which has a melting point of 180°–185° C. and an epoxide equivalent weight of 178.0.

C. Characterization of the Diglycidyl Ether of 4,4'-Dihydroxybenzanilide for Liquid Crystal Character A sample of the diglycidyl ether of 4,4'-dihydroxybenzanilide prepared in B is heated on a hot stage under an optical microscope (70× magnification) using a cross polarized light source. Melting and clearing to an isotropic state is observed between 179°-185° C. Upon cooling from 185° C., the development of a birefringent phase is first observed at 165° C. which is completed at 160° C. In this temperature range, the resin is still fluid. On further cooling, the resin is observed to crystallize at approximately 150° C.

Differential scanning calorimetry analysis of the diglycidyl ether of 4,4'-dihydroxybenzanilide at a heating rate of 20° C. per minute shows a small endotherm (14 joules/gram) between 150°-170° C. followed by a melt endotherm at 183° C. On cooling at 20° C. per minute, a small broad exotherm is observed between 180° and 148° C. followed by a larger exotherm beginning at 148° C. (−50 joules/gram). These observed transitions change with repeated heating and cooling which is attributed to the slow self-cure of the diglycidyl ether of 4,4'-dihydroxybenzanilide at these temperatures.

EXAMPLE 5

A. Microscopic Observations During Cure of the Diglycidyl Ether of 4,4'-Dihydroxy-alpha-methylstilbene with 4,4'-Diaminostilbene A portion (0.4469 grams) of the diglycidyl ether of 4,4'-dihydroxy-alpha-methylstilbene from Example 3-B is combined with an equivalent amount (0.1315 grams) of 4,4'-diaminostilbene from Example 1-C. These compounds are ground together to form a fine, homogeneous powder. A sample of this mixture is placed on a hot stage which has been heated to 160° C. and then observed via optical microscopy under crosspolarized light at 70× magnification. At the 160° C. temperature, a non-birefringent melt occurs in less than one minute. After three minutes at 160° C., the hot stage is cooled to 150° C. over a one minute period. During the cooling to 150° C., a birefringent phase having a liquid crystalline appearance is observed to form. At this stage of cure, further heating to 225° C. at a rate of 10° C. per minute has no visually observable effect on the ordered morphology produced by the cooling from 160° C. to 150° C.

B. Preparation of a Neat Resin Casting of the Diglycidyl Ether of 4,4'-Dihydroxy-alpha-methylstilbene Cured with 4,4'-Diaminostilbene A portion (2.9285 grams) of the diglycidyl ether of 4,4'-dihydroxy-alpha-methylstilbene from Example 3-B is combined with an equivalent amount (0.8708 grams) of 4,4'-diaminostilbene from Example 1-C. These compounds are ground together to form a fine, homogeneous powder and then transferred to an aluminum cup. The aluminum cup containing this mixture is placed in an oven which has been heated to 160° C. Melting to a translucent liquid occurs after several stirrings with a spatula. After six minutes at 160° C., thickening of the resin and stir opalescence are observed. At this time, the oven temperature is reduced to 150° C. followed by the resin becoming opaque and gelatinous. After three hours at the 150° C. temperature, the oven temperature is increased to 180° C. and held therein for one hour, then 210° C. and held therein for one hour. The oven temperature is then increased to 230° C. where it is held for three hours before cooling to room temperature (24° C.). At room temperature an opaque casting is removed from the aluminum cup. The edges of the casting exhibited a high level of birefringence when observed via optical light microscopy under crosspolarized light at 70× magnification. Differential scanning calorimetry of a portion (15 milligrams) of the casting using a heating rate of 10° C. per minute from 30° to 300° C. reveals the presence of no glass transition temperature and no residual cure energy. The results are reported in Table III.

EXAMPLE 6

A. Microscopic Observations During Cure of the Diglycidyl Ether of 4,4'-Dihydroxybenzanilide with 4,4'-Diaminobenzanilide A portion (0.1403 grams) of the diglycidyl ether of 4,4'-dihydroxybenzanilide from Example 4-B is combined with an equivalent amount (0.0448 grams) of 4,4'-diaminobenzanilide from Example 2-B. These compounds are ground together to form a fine, homogeneous powder. A sample of this mixture is placed on a hot stage which had been heated to 150° C. and then observed via optical microscopy under crosspolarized light at 70× magnification. At the 150° C. temperature, a non-birefringent melt occurred in less than one minute. After two minutes, the formation of a birefringent phase having a liquid crystalline appearance is observed to form. With the formation of the birefringent phase, the resin set to a solid within one minute. At this stage of cure, further heating to 225° C. at a rate of 10° C. per minute has no visually observable effect on the ordered morphology produced at 150° C.

B. Preparation of a Neat Resin Casting of the Diglycidyl Ether of 4,4'-Dihydroxybenzanilide Cured with 4,4'-Diaminobenzanilide A portion (3.0452 grams) of the diglycidyl ether of 4,4'-dihydroxybenzanilide from Example 4-B is combined with an equivalent amount (0.9721 grams) of 4,4'-diaminobenzanilide from Example 2-B. These compounds are ground together to form a fine, homogeneous powder and then transferred to an aluminum cup. The aluminum cup containing this mixture is placed in an oven which had been heated to 150° C. Melting to a translucent liquid occurs after several stirrings with a spatula. After six minutes at 160° C. the resin become gelatinous. After three hours at the 160° C. temperature, the oven temperature is increased to 180° C. and held therein for one hour, then 210° C. and held therein for one hour. The oven temperature is then increased to 230° C. where it is held for three hours before cooling to room temperature (24° C.). At room temperature an opaque casting is removed from the aluminum cup. The edges of the casting exhibits a high level of birefringence when observed via optical light microscopy under crosspolarized light at 70× magnification. Differential scanning calorimetry of a portion (15 milligrams) of the casting using a heating rate of 10° C. per minute from 30° to 300° C. reveals the presence of no glass transition temperature and no residual cure energy. The results are reported in Table III.

COMPARATIVE EXPERIMENT A

1. Microscopic Observations During Cure of the Diglycidyl Ether of 4,4'-Isopropylidenediphenol with 4,4'-Diaminostilbene A portion (3.0549 grams) of the diglycidyl ether of 4,4'-isopropylidenediphenol having an epoxide equivalent weight of 179.5 is combined with an equivalent amount (0.8948 grams) of 4,4'-diaminostilbene from Example 1-C. These compounds are mixed together in an aluminum cup to form a homogeneous thick paste. A sample of this mixture is placed on a hot stage which had been heated to 160° C. and then observed via optical microscopy under crosspolarized light at 70× magnification. At the 160° C. temperature, the 4,4'-diaminostilbene is observed to dissolve into the diglycidyl ether of 4,4'-isopropylidenediphenol in less than one minute to form a non-birefringent liquid. After six minutes, the resin set to a non-birefringent solid. The solid is cooled to room temperature at a rate of 10° C. per minute and again observed via optical microscopy under crosspolarized light to reveal a lack of birefringence.

2. Preparation of a Neat Resin Casting of the Diglycidyl Ether of 4,4'-Isopropylidenediphenol Cured with 4,4'-Diaminostilbene The aluminum cup containing the remaining mixture of diglycidyl ether of 4,4'-isopropylidenediphenol and 4,4'-diaminostilbene from A above is placed in an oven which has been heated to 160° C. At the 160° C. temperature, all of the 4,4'-diaminostilbene is observed to dissolve into the diglycidyl ether of 4,4'-isopropylidenediphenol after six minutes with several stirrings with a spatula. At this time, the oven temperature is reduced to 150° C. followed by the resin becoming gelatinous two minutes later. After three hours at the 150° C. temperature, the oven temperature is increased to 180° C. and held therein for one hour, then 210° C. and held therein for one hour. The oven temperature is then increased to 230° C. where it is held for three hours before cooling to room temperature (24° C.). At room temperature a translucent casting is removed from the aluminum cup. The casting exhibits a low level of birefringence when observed via optical light microscopy under crosspolarized light at 70× magnification. Differential scanning calorimetry of a portion (15 milligrams) of the casting using a heating rate of 10° C. per minute from 30° to 300° C. reveals a glass transition temperature of 204° C. and no residual cure energy. The results are reported in Table III.

COMPARATIVE EXPERIMENT B

1. Microscopic Observations During Cure of the Diglycidyl Ether of 4,4'-Isopropylidenediphenol with 4,4'-Diaminobenzanilide A portion (3.0198 grams) of the diglycidyl ether of 4,4'-isopropylidenediphenol having an epoxide equivalent weight of 179.5 is combined with an equivalent amount (0.9560 grams) of 4,4'-diaminobenzanilide from Example 2-B. These compounds are mixed together in an aluminum cup to form a homogeneous thick paste. A sample of this mixture is placed on a hot stage which has been heated to 150° C. and then observed via optical microscopy under crosspolarized light at 70× magnification. At the 150° C. temperature, the 4,4'-diaminobenzanilide is observed to dissolve into the diglycidyl ether of 4,4'-isopropylidenediphenol in less than one minute to form a non-birefringent liquid. After eight minutes, the resin set to a non-birefringent solid. The solid is cooled to room temperature at a rate of 10° C. per minute and again observed via optical microscopy under crosspolarized light to reveal a lack of birefringence.

2. Preparation of a Neat Resin Casting of the Diglycidyl Ether of 4,4'-Isopropylidenediphenol Cured with 4,4'-Diaminobenzanilide The aluminum cup containing the remaining mixture of diglycidyl ether of 4,4'-isopropylidenediphenol and 4,4'-diaminobenzanilide from A above is placed in an oven which has been heated to 150° C. At the 150° C. temperature, all of the 4,4'-diaminobenzanilide is observed to dissolve into the diglycidyl ether of 4,4'-isopropylidenediphenol after eleven minutes with several stirrings with a spatula. After five minutes at 150° C., the resin became gelatinous. After three hours at the 150° C. temperature, the oven temperature is increased to 180° C. and held therein for one hour, then 210° C. and held therein for one hour. The oven temperature is then increased to 230° C. where it is held for three hours before cooling to room temperature (24° C.). At room temperature a translucent casting is removed from the aluminum cup. The casting exhibits a low level of birefringence when observed via optical light microscopy under crosspolarized light at 70× magnification. Differential scanning calorimetry of a portion (15 milligrams) of the casting using a heating rate of 10° C. per minute from 30° to 300° C. reveals a glass transition temperature of 210° C. and no residual cure energy. The results are reported in Table III.

TABLE III

| Property Evaluated | Designation of Resin System | | | |
| --- | --- | --- | --- | --- |
| | Example 5 | Example 6 | Comparative Experiment A | Comparative Experiment B |
| Morphology produced during cure (via microscopic observation) | birefringent | birefringent | non-birefringent | non-birefringent |
| Glass transition temperature of cured resin (via differential scanning calorimetry) | none detected below 300° C. | none detected below 300° C. | 204° C. | 210° C. |

What is claimed is:

1. A curable composition comprising (A) one or more epoxy resins containing one or more rodlike mesogenic moieties represented by the following Formula I

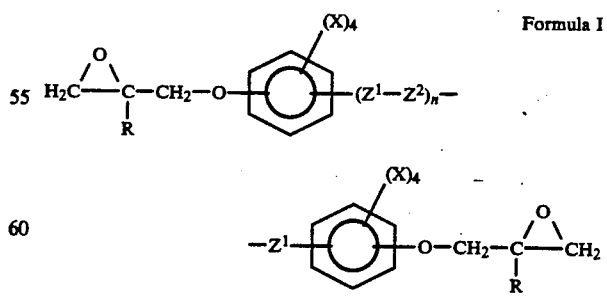

Formula I wherein at least about 80 percent of the —($Z^1$—$Z^2$)$_n$—$Z^1$— linkages and the glycidyl ether groups are in the para position with respect to each other; each R and $R^1$ is independently hydrogen or an aliphatic hydrocarbon group having from 1 to about 4 carbon atoms; each X is independently hydrogen, a hydrocarbyl or hydrocarbyloxy group having suitably from 1 to about 12 carbon atoms, a halogen atom, —NO$_2$, or —C≡N; each Z$^1$ is independently —CR$^1$=CR$^1$—, —CR$^1$=CR$^1$—CR$^1$=CR$^1$—, —CR$^1$=N—N=CR$^1$—, —CR$^1$=CR$^1$—CO—O—CH$_2$—, —CR$^1$=CR$^1$—CO—O—CH$_2$—CH$_2$—, —CH$_2$—O—CO—CR$^1$=CR$^1$—, —CH$_2$—CH$_2$—O—CO—CR$^1$=CR$^1$—, —CR$^1$=CR$^1$—CO—O—, —O—CO—CR$^1$=CR$^1$—, —CO—NR$^1$—, —NR$^1$—CO—, —CO—NR$^1$—NR$^1$—CO—, —C≡C—, —C≡C—C≡C—, —CR$^1$=CR$^1$—O—CO—CH$_2$—, —CH$_2$—CO—O—CR$^1$=CR$^1$—, —CR$^1$=CR$^1$—O—CO—CH$_2$—CH$_2$—, —CH$_2$—CH$_2$—CO—O—CR$^1$=CR$^1$—, —CH$_2$—CH$_2$—CO—O—, —O—CO—CH$_2$—CH$_2$—, —CO—O—CR$^1$=CR$^1$—, —CR$^1$=CR$^1$—O—CO—,

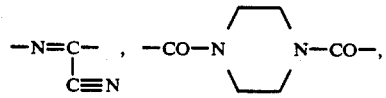

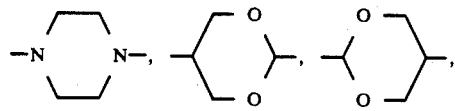

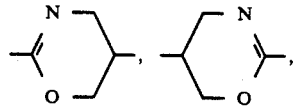

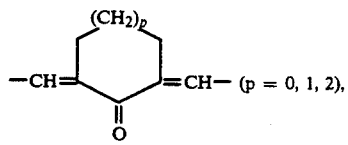

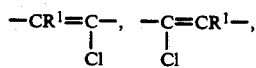

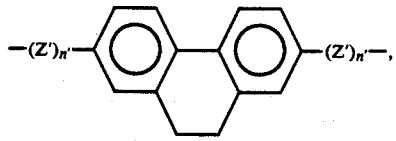

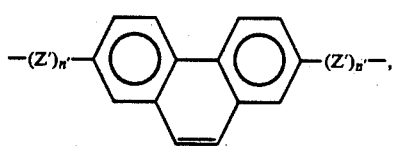

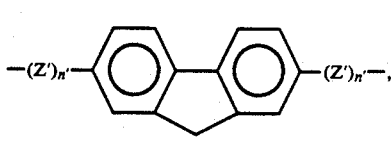

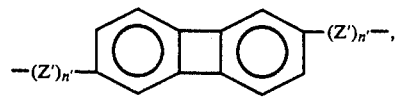

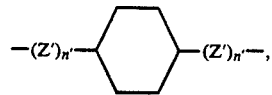

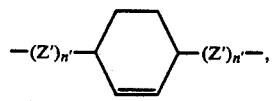

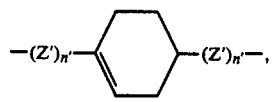

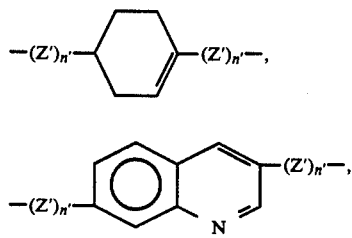

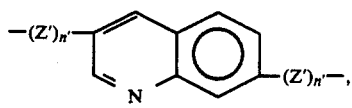

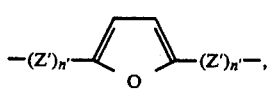

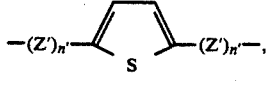

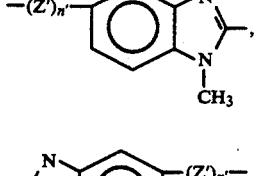

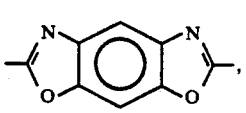

-continued

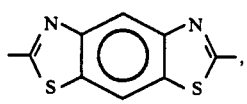

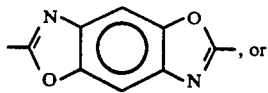, or

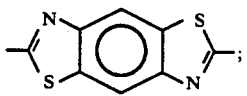;

$Z^2$ is a group represented by a cyclic or bicyclic ring system containing from 5 to about 12 carbon atoms and may be cycloaliphatic, polycycloaliphatic, aromatic or a combination thereof; n is 0 to 2; each $Z'$ is independently a —CO—, —O—CO—, —CO—O—, —CO—NR$^1$—, or —NR$^1$—CO— group and each n' independently has a value of zero or one;

with the proviso that:

(a) both of the $R^1$ groups in the —CR$^1$=CR$^1$— group cannot simultaneously be a hydrogen atom;

(b) each $Z^1$ can also independently be

—CR$^1$=N—, —N=CR$^1$—, —CO—CR$^1$=CR$^1$— and —CR$^1$=CR$^1$—CO— when $Z^2$ is not a benzene ring and n≠0;

(c) $R^1$ in the —CR$^1$=N— and —N=CR$^1$— groups is other than hydrogen;

(d) when n=1, either one of $Z^1$ can also be selected from the group consisting of —CH=CH—, —N=N—, —CO—S—, —S—CO—, —CH=N—, —N=CH—, —O—CO—, —CO—O— and a direct single bond provided that the other $Z^1$ group is not selected from this same group or is not selected from a group selected from the group consisting of

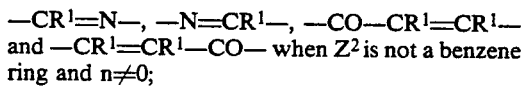

,

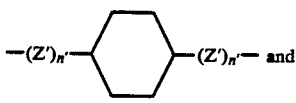 and when (i) each n' is zero, or (ii) when one n'=zero and one n'=1 with $Z'$ being —O—CO— or —CO—O— and $R^1$ is a group having only one carbon atom;

(e) when n=2, one or two $Z^1$ groups can also independently be selected from the group consisting of —CH=CH—, —N=N—, —CO—S—, —S—CO—, —CH=N—, —N=CH—, —O—CO—, —CO—O—, and a direct single bond, provided that the remaining $Z^1$ groups are not selected from this group;

(f) when one $Z^1$ is

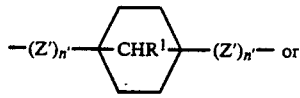 or

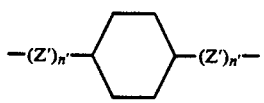

wherein (i) when each n'=1 with each $Z'$ being —O—CO— or —CO—O—, or (ii) when one n'=1 with $Z'$ being —O—CO— or —CO—O— and the other n'=zero resulting in the other $Z'$ being a direct bond and $R^1$ is a group having only one carbon atom, then n must have a value of 1 or 2 and $R^1$ is a group having only one carbon atom; and (B) a curing amount of one or more polyamines containing one or more rodlike mesogenic moieties.

2. A curable composition of claim 1 wherein when X is a hydrocarbyl or hydrocarbyloxy group, it has from 1 to about 6 carbon atoms and when it is a halogen atom, it is chlorine or bromine.

3. A curable composition of claim 1 wherein when X is a hydrocarbyl or hydrocarbyloxy group, it has from 1 to about 4 carbon atoms and when it is a halogen atom, it is bromine.

4. A curable composition comprising (A) one or more epoxy resins containing one or more rodlike mesogenic moieties represented by the following Formula II

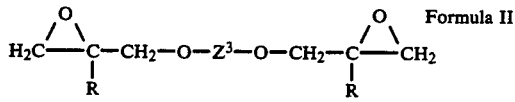 Formula II wherein $Z^3$ is

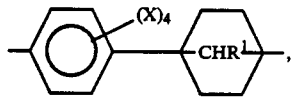,

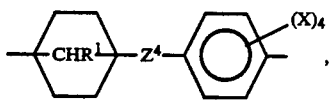, and $Z^4$ is —CO—O—, —O—CO—, —NR$^1$—CO— or —CO—NR$^1$—; and $X^1$ is a divalent hydrocarbyl group having from 1 to about 10, carbon atoms which can contain one or more heteroatoms selected from N, O or S and may be saturated or unsaturated; each R and $R^1$ is independently hydrogen or

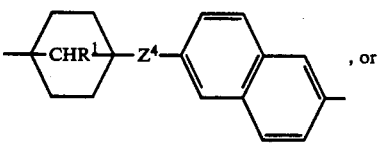, or

-continued

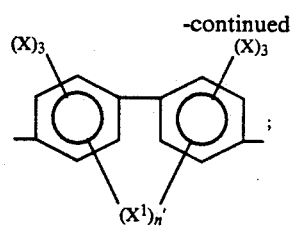

an aliphatic hydrocarbon group having from 1 to about 4 carbon atoms; each X is independently hydrogen, a hydrocarbyl or hydrocarbyloxy group having from 1 to about 12 carbon atoms, a halogen atom, $-NO_2$, or $-C\equiv N$; and n' is zero or one; and with the proviso that $Z^4$ is not $-CO-O-$ or $-O-CO-$ when $R^1$ is a group having only one carbon atom; and (B) a curing amount of one or more polyamines containing one or more rodlike mesogenic moieties.

5. A curable composition of claim 4 wherein when X is a hydrocarbyl or hydrocarbyloxy group, it has from 1 to about 6 carbon atoms and when it is a halogen atom, it is chlorine or bromine.

6. A curable composition of claim 4 wherein when X is a hydrocarbyl or hydrocarbyloxy group, it has from 1 to about 4 carbon atoms and when it is a halogen atom, it is bromine.

7. A curable composition comprising (A) the diglycidyl ether of 4,4'-dihydroxy-α-methylstilbene, the diglycidyl ether of 4,4'-dihydroxybenzanilide, or a mixture thereof; and (B) a curing amount of one or more polyamines containing one or more rodlike mesogenic moieties.

8. A curable composition comprising (I) a blend comprising
(A) one or more epoxy resins or monoepoxide compounds containing one or more rodlike mesogenic moieties represented by either the following Formula I

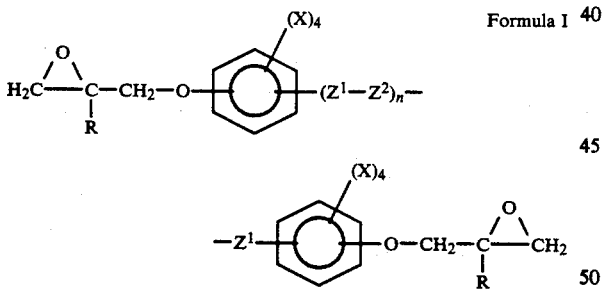

Formula I wherein at least about 80 percent of the $-(Z^1-Z^2)_n-Z^1-$ linkages and the glycidyl ether groups are in the para position with respect to each other; each R and $R^1$ is independently hydrogen or an aliphatic hydrocarbon group having from 1 to about 4 carbon atoms; each X is independently hydrogen, a hydrocarbyl or hydrocarbyloxy group having from 1 to about 12 carbon atoms, a halogen atom, $-NO_2$, or $-C\equiv N$, each $Z^1$ is independently $-CR^1=CR^1-$, $-CR^1=CR^1-CR^1=CR^1-$, $CR^1=N-N=CR^1-$, $-CR^1=CR^1-CO-O-CH_2-$, $-CR^1=CR^1-CO-O-CH_2-CH_2-$, $-CH_2-O-CO-CR^1=CR^1-$, $-CH_2-CH_2-O-CO-CR^1=CR^1-$, $-CR^1=CR^1-CO-O-$, $-O-CO-CR^1=CR^1-$, $-CO-NR^1-$, $-NR^1-CO-$, $-CO-NR^1-CO-$, $-NR^1-CO-$, $-C\equiv C-$, $-C\equiv C-C\equiv C-$, $-CR^1=CR^1-O-CO-CH_2-$, $CH_2-CO-O-CR^1=CR^1-$, $-CR^1=CR^1-O-CO-CH_2-CH_2-$, $-CH_2-CH_2-CO-O-CR^1=CR^1-$, $-CH_2-CH_2-CO-O-$, $-O-CO-CH_2-CH_2-$, $-CO-O-CR^1=CR^1-$, $-CR^1=CR^1-O-CO-$,

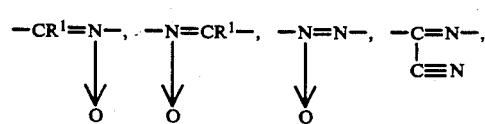

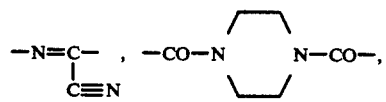

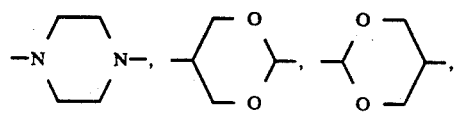

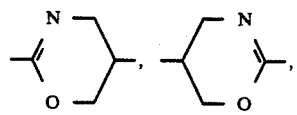

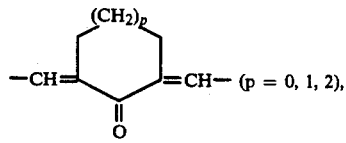

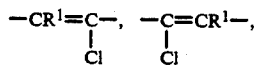 ($p = 0, 1, 2$),

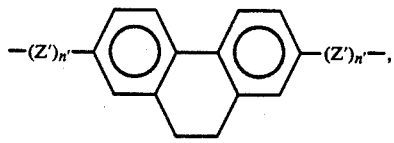

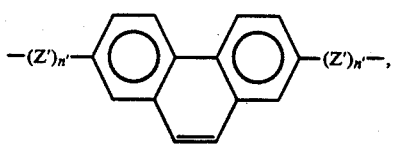

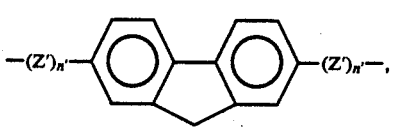

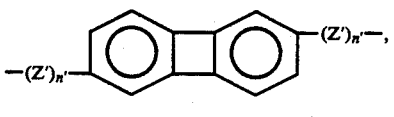

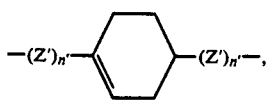

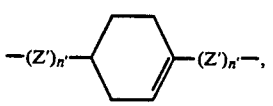

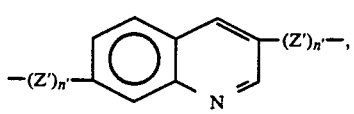

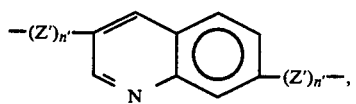

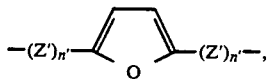

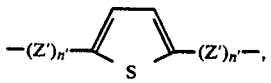

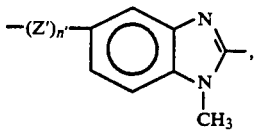

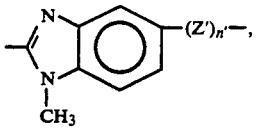

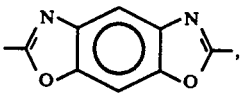

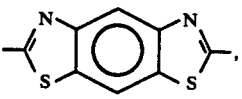

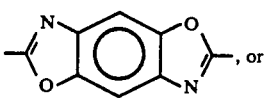

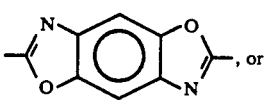, or

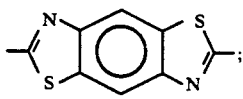

$Z^2$ is a group represented by a cyclic or bicyclic ring system containing from 5 to about 12 carbon atoms and may be cycloaliphatic, polycycloaliphatic, aromatic or a combination thereof; n is 0 to 2; each $Z'$ is independently a —CO—, —O—CO—, —CO—O—, —CO—NR$^1$—, or —NR$^1$—CO— group and each n' independently has a value of zero or one; with the proviso that:

(a) both of the R$^1$ groups in the —CR$^1$=CR$^1$— group cannot simultaneously be a hydrogen atom;

(b) each $Z^1$ can also independently be

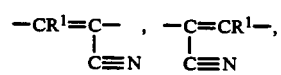

—CR$^1$=N—, —N=CR$^1$—, —CO—CR$^1$=CR$^1$— and —CR$^1$=CR$^1$—CO— when $Z^2$ is not a benzene ring and n≠0;

(c) R$^1$ in the —CR$^1$=N— and —N=CR$^1$— groups is other than hydrogen;

(d) when n=1, either one of $Z^1$ can also be selected from the group consisting of —CH=CH—, —N=N—, —CO—S—, —S—CO—, —CH=N—, —N=CH—, —O—CO—, —CO—O— and a direct single bond provided that the other $Z^1$ group is not selected from this same group or is not selected from a group selected from the group consisting of

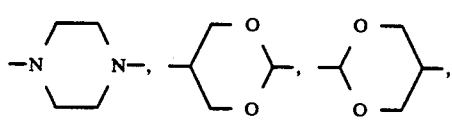

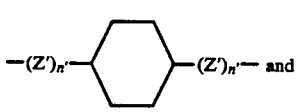 and when (i) each n' is zero, or (ii) when one n'=zero and one n'=1 with Z' being —O—CO— or —CO—O— and R$^1$ is a group having only one carbon atom;

(e) when n=2, one or two $Z^1$ groups can also independently be selected from the group consisting of —CH=CH—, —N=N—, —CO—S—, —S—CO—, —CH=N—, —N=CH—, —O—CO—, —CO—O—, and a direct single bond, provided that the remaining $Z^1$ groups are not selected from this group;

(f) when one $Z^1$ is

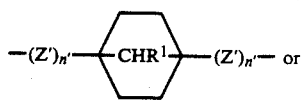

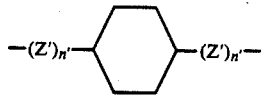

wherein (i) when each n'=1 with each Z' being —O—CO— or —CO—O—, or (ii) when one n'=1 with Z' being —O—CO— or —CO—O— and the other n'=zero resulting in the other Z' being a direct bond and $R^1$ is a group having only one carbon atom, then n must have a value of 1 or 2 and $R^1$ is a group having only one carbon atom; or the following Formula II

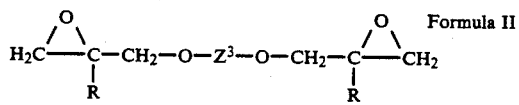

wherein $Z^3$ is

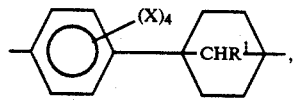

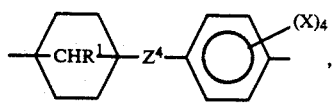

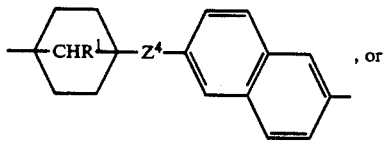, or

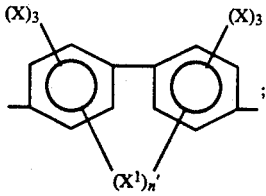;

and $Z^4$ is —CO—O—, —O—CO—, —NR$^1$—CO— or —CO—NR$^1$—; and $X^1$ is a divalent hydrocarbyl group having from 1 to about 10 carbon atoms which can contain one or more heteroatoms selected from N, O or S and may be saturated or unsaturated; each R and $R^1$ is independently hydrogen or an aliphatic hydrocarbon group having from 1 to about 4 carbon atoms; each X is independently hydrogen, a hydrocarbyl or hydrocarbyloxy group having from 1 to about 12 carbon atoms, a halogen atom, —NO$_2$, or —C≡N; and n' is zero or one; and with the proviso that $Z^4$ is not —CO—O— or —O—CO— when $R^1$ is a group having only one carbon atom; or the following Formula III

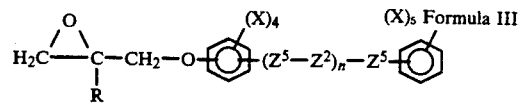

wherein at least about 80 percent of the —($Z^5$-$Z^2$)$_n$—$Z^5$— linkages and the glycidyl ether groups are in the para position with respect to each other; each R and $R^1$ is independently hydrogen or an aliphatic hydrocarbon group having from 1 to about 4 carbon atoms; each X is independently hydrogen, a hydrocarbyl or hydrocarbyloxy group having from 1 to about 12 carbon atoms, a halogen atom, —NO$_2$, or —C≡N; each $Z^5$ is independently —CR$^1$=CR$^1$—, —CR$^1$=CR$^1$—CR$^1$=CR$^1$—, —CR$^1$=N—N=CR$^1$, —CR$^1$=C-R$^1$—CO—O—CH$_2$—, —CR$^1$=C-R$^1$—CO—O—CH$_2$—CH$_2$—, —CH$_2$—O—CO—CR$^1$=CR$^1$—, —CH$_2$—CH$_2$—O—CO—CR$^1$=CR$^1$—, —CR$^1$=C-R$^1$—CO—O—, —O—CO—CR$^1$=CR$^1$—, —N=N—, —CO—NR$^1$—, —NR$^1$—CO—, —CO—NR$^1$—NR$^1$—CO—, —C≡C—, —C≡C—C≡C—, —CO—S—, —S—CO—, —CR$^1$=N—, —N=CR$^1$—, —CO—O—, —O—CO—, —CR$^1$=CR$^1$—O—CO—CH$_2$—, —CH$_2$—CO—O—CR$^1$=CR$^1$—, —CR$^1$=C-R$^1$—O—CO—CH$_2$—CH$_2$—, —CH$_2$—CH$_2$—CO—O—CR$^1$=CR$^1$—, —CH$_2$—CH$_2$—CO—O—, —O—CO—CH$_2$—CH$_2$—CH$_2$—, —CO—O—CR$^1$=CR$^1$—, —CR$^1$=C-R$^1$—O—CO—, a direct single bond when n≧1,

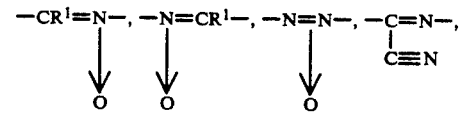

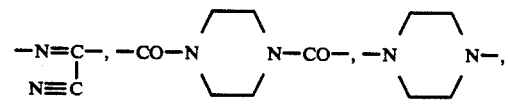

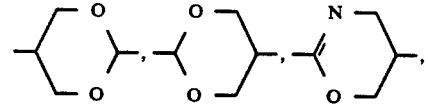

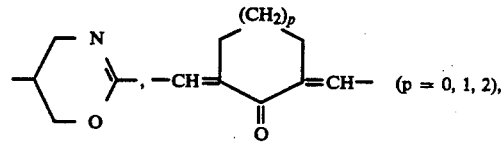 (p = 0, 1, 2),

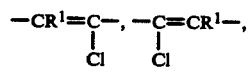

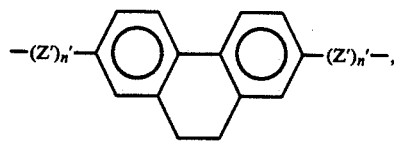

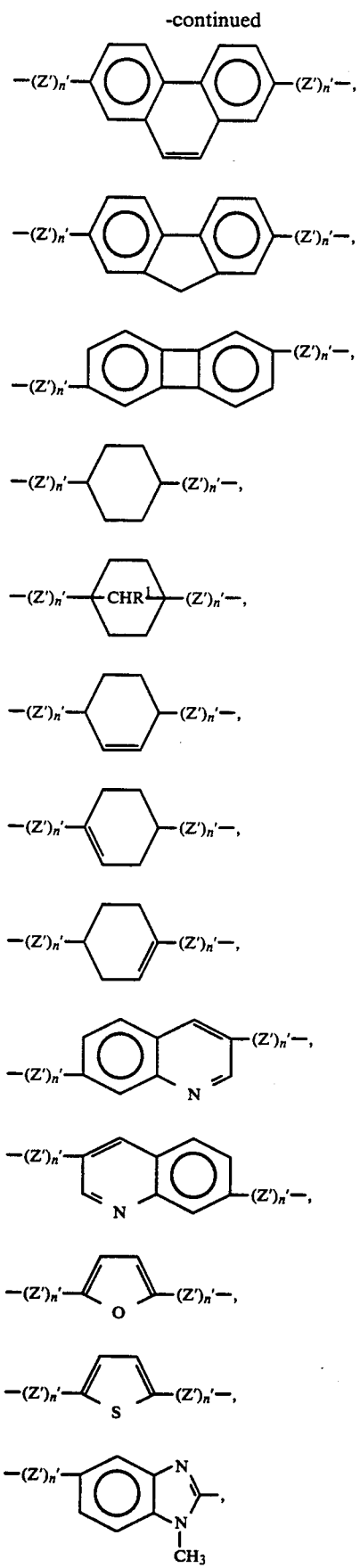
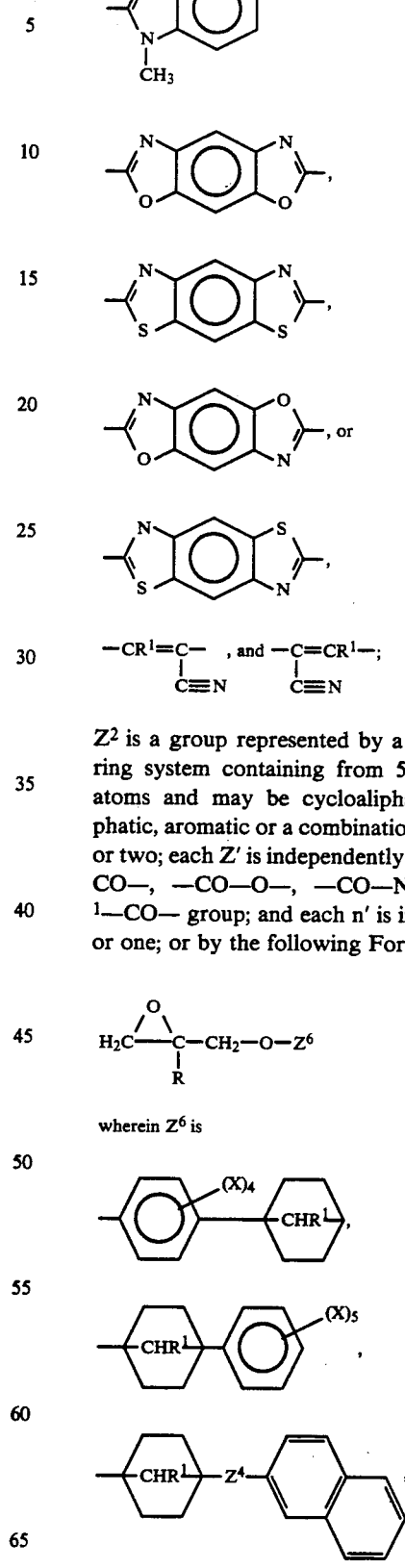
$Z^2$ is a group represented by a cyclic or bicyclic ring system containing from 5 about 12 carbon atoms and may be cycloaliphatic, polycycloaliphatic, aromatic or a combination thereof; n is zero or two; each $Z'$ is independently a —CO—, —O—CO—, —CO—O—, —CO—NR$^1$—, or —NR$^1$—CO— group; and each n' is independently zero or one; or by the following Formula IV
Formula IV
wherein $Z^6$ is -continued

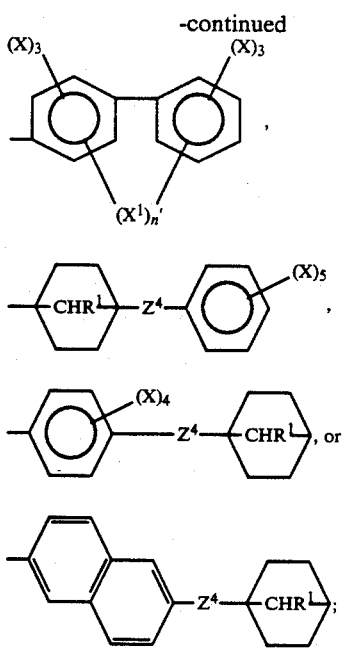

$Z^4$ is —CO—O—, —O—CO—, —NR$^1$—CO— or —CO—NR$^1$—; each R and R$^1$ is independently hydrogen or an aliphatic hydrocarbon group having from 1 to about 4 carbon atoms; each X is independently hydrogen, a hydrocarbyl or hydrocarbyloxy group having from 1 to about 12 carbon atoms, a halogen atom, —NO$_2$, or —C≡N; X$^1$ is a divalent hydrocarbyl group having from 1 to about 10 carbon atoms which can contain one or more heteroatoms selected from N, O or S and may be saturated or unsaturated; and n' is zero or one; or any combination of any two or more epoxy resins or monoepoxide compounds represented by the aforementioned Formulas I, II, III and IV;

(B) one or more polyepoxides which are substantially free or rodlike mesogenic moieties; and (II) a curing amount of one or more polyamines containing one or more rodlike mesogenic moieties.

9. A curable composition of claim 8 wherein;

(a) when component (A) is an epoxy resin represented by Formula I and when X therein is a hydrocarbyl or hydrocarbyloxy group, it has from 1 to about 6 carbon atoms and when it is a halogen atom, it is chlorine or bromine;

(b) when component (A) is an epoxy resin represented by Formula II and when X therein is a hydrocarbyl or hydrocarbyloxy group, it has from 1 to about 6 carbon atoms and when it is a halogen atom, it is chlorine or bromine;

(c) component (B) is an epoxy resin represented by the following Formulas V, VI, VII, VIII, IX, X or XI

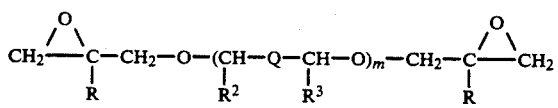

Formula V

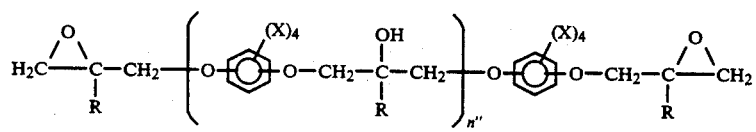

Formula VI

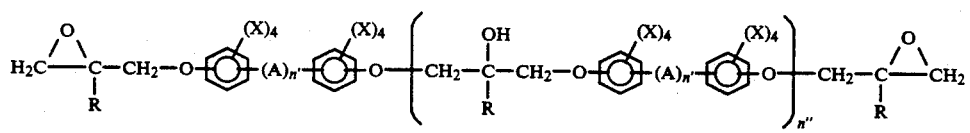

Formula VII

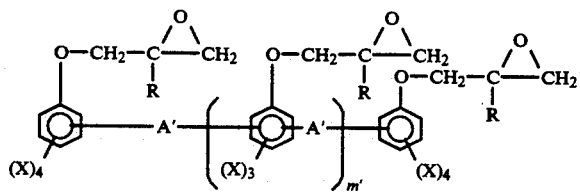

Formula VIII

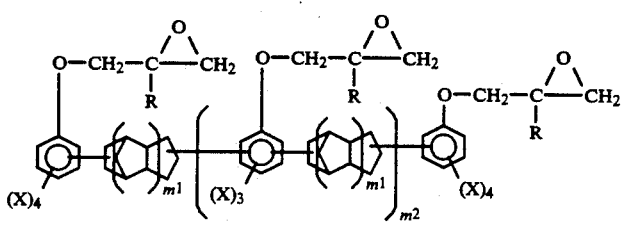

Formula IX

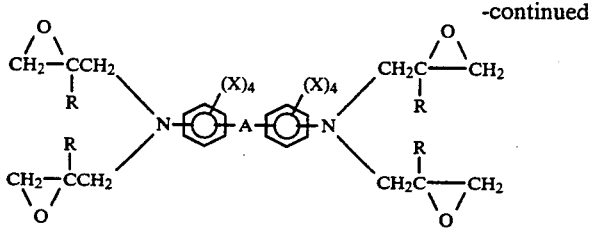
Formula X

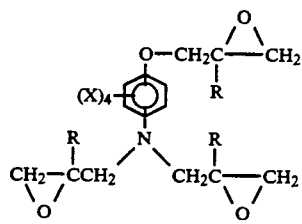
Formula XI wherein each A is independently a divalent hydrocarbyl group having from 1 to about 12 carbon atoms, —O—, —S—, —S—S—, —SO—, —SO$_2$—, or —CO—; each A' is independently a divalent hydrocarbon group having from 1 to about 6 carbon atoms; Q is a single bond, —CH$_2$—S—CH$_2$—, —(CH$_2$)$_{n1}$—, or

each R is independently hydrogen or an alkyl group having from 1 to about 4 carbon atoms; each R$^2$ and R$^3$ is independently hydrogen, a hydrocarbyl or halohydrocarbyl group having from 1 to about 6 carbon atoms; each X is independently hydrogen, a hydrocarbyl or hydrocarbyloxy group having from 1 to about 12, carbon atoms, a halogen atom, —NO$_2$ or —C≡N; m has a value from about 1 to about 10; m' has an average value from about 0.01 to about 12; m$^1$ has an average value from about 1 to about 12; m$^2$ has a value from about 1 to about 12; n' has a value of zero or 1; n" has an average value from about zero to about 3 and n$^1$ has an average value from about 1 to about 10; and (d) component (A) is present in an amount of from about 1 to about 99 percent by weight based on the combined quantities of components (A) and (B); and component (B) is present in an amount of from about 99 to about 1 percent by weight based on the combined quantities of components (A) and (B).

10. A curable composition of claim 9 wherein;
(a) when component (A) is an epoxy resin represented by Formulas I or II and when X is a hydrocarbyl or hydrocarbyloxy group, it has from 1 to about 4 carbon atoms and when it is a halogen atom, it is bromine; and
(b) component (A) is present in an amount of from about 10 to about 80 percent by weight based on the combined quantities of components (A) and (B); and component (B) is present in an amount of from about 90 to about 20 percent by weight based on the combined quantities of components (A) and (B).

11. A curable composition of claim 10 wherein component (A) is present in an amount of from about 10 to about 50 percent by weight based on the combined quantities of components (A) and (B); and component (B) is present in an amount of from about 90 to about 50 percent by weight based on the combined quantities of components (A) and (B).

12. A curable composition of claim 11 wherein component (B) is a diglycidyl ether of bisphenol A, a diglycidyl ether of 4,4'-dihydroxydiphenyl methane, a diglycidyl ether of 4,4'-dihydroxybenzophenone, a diglycidyl ether of 4,4'-dihydroxythiodiphenol, a diglycidyl ether of 1,1-bis(4-hydroxylphenyl)-1-phenyl ethane (bisphenol AP), or an combination thereof.

13. A curable composition of claim 12 wherein component (A) is a diglycidyl ether of 4,4'-dihydroxy-α-methylstilbene or a diglycidyl ether of 4,4'-dihydroxybenzanilide.

14. A curable composition comprising
(I) a blend comprising
(A) one or more epoxy resins containing an average of more than one vicinal epoxide group per molecule and one or more rodlike mesogenic moieties per molecule; and
(B) one or more compounds containing only one vicinal epoxide group per molecule and one or more rodlike mesogenic moieties per molecule; and
(II) at least one polyamine containing one or more rodlike mesogenic moieties.

15. A curable composition of claim 14 wherein
(a) said epoxy resins containing an average of more than one vicinal epoxide group per molecule and one or more rodlike mesogenic moieties per molecule are those represented by the following Formula I

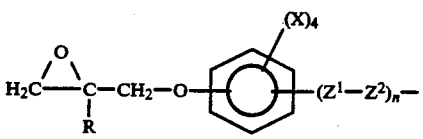
Formula I

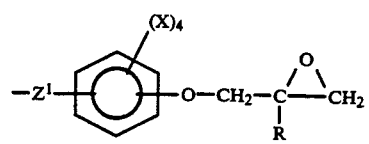

wherein at least about 80 percent of the —($Z^1$-$Z^2$-)$_n$—$Z^1$— linkages and the glycidyl ether groups are in the para position with respect to each other; each R and $R^1$ is independently hydrogen or an aliphatic hydrocarbon group having from 1 about 4 carbon atoms; each X is independently hydrogen, a hydrocarbyl or hydrocarbyloxy group having from 1 to about 12 carbon atoms, a halogen atom, —$NO_2$, or —C≡N; each $Z^1$ is independently —$CR^1$=$CR^1$—, —$CR^1$=$CR^1$—$CR^1$=$CR^1$—, —$CR^1$=N—N=$CR^1$, —$CR^1$=$CR^1$—CO—O—$CH_2$—, —$CR^1$=$CR^1$—CO—O—$CH_2$—$CH_2$—, —$CH_2$—O—CO—$CR^1$=$CR^1$—, —$CH_2$—$CH_2$—O—CO—$CR^1$=$CR^1$—, —$CR^1$=$CR^1$—CO—O—, —O—CO—$CR^1$=$CR^1$—, —CO—$NR^1$—, —$NR^1$—CO—, —CO—$NR^1$—$NR^1$—CO—, —C≡C—, —C≡C—C≡C—, —N=N—, —CO—S—, —S—CO—, —$CR^1$=N—, —N=$CR^1$—, —CO—$CR^1$=$CR^1$—, —$CR^1$=$CR^1$—, —$CR^1$=$CR^1$—O—CO—$CH_2$—, —$CH_2$—CO—O—$CR^1$=$CR^1$—, —$CR^1$=$CR^1$—O—CO—$CH_2$—$CH_2$—, —$CH_2$—$CH_2$—CO—O—$CR^1$=$CR^1$—, —$CH_2$—$CH_2$—CO—O—, —O—CO—$CH_2$—$CH_2$—$CH_2$—, —CO—O—$CR^1$=$CR^1$—, —$CR^1$=$CR^1$—O—CO—,

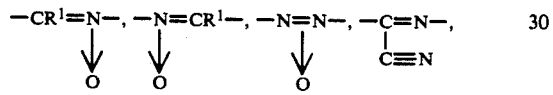

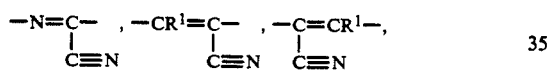

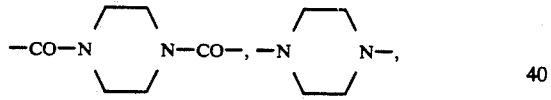

—CO—N⌒N—CO—, —N⌒N—,

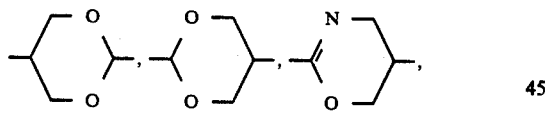

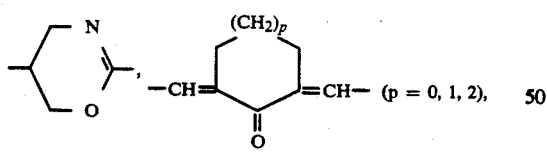 —CH=⌬=CH— (p = 0, 1, 2),

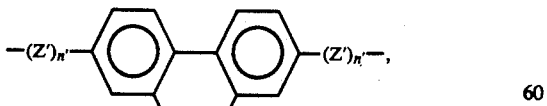

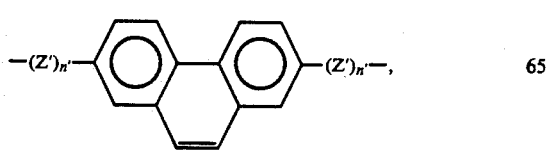

-continued

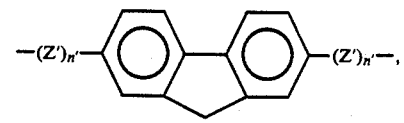

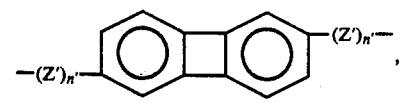

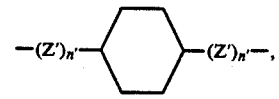

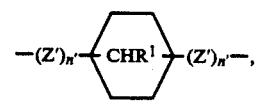

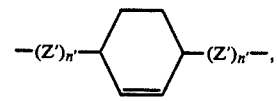

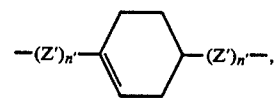

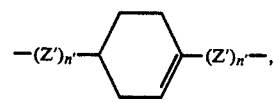

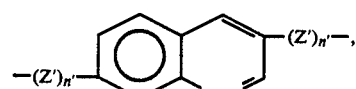

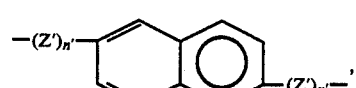

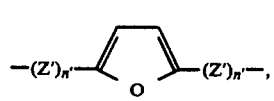

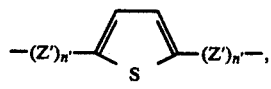

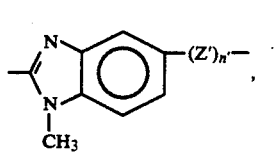

-continued

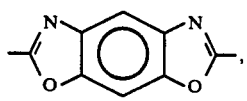

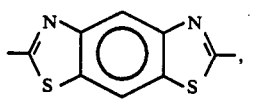

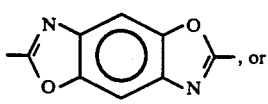

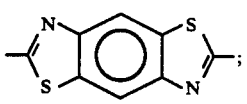

$Z^2$ is a group represented by a cyclic or bicyclic ring system containing from 5 to about 12 carbon atoms and may be cycloaliphatic, polycycloaliphatic, aromatic or a combination thereof; n is 0 to 2; each $Z'$ is independently a —CO—, —O—CO—, —CO—O—, —CO—NR$^1$—, or —NR$^1$—CO— group and each n' independently has a value of zero or one; or the following Formula II

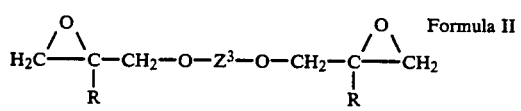

wherein $Z^3$ is

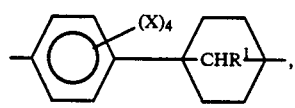

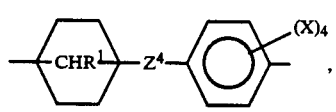

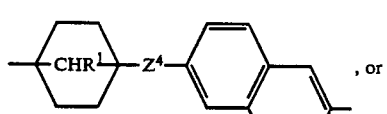

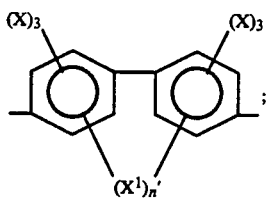

and $Z^4$ is —CO—O—, —O—CO—, —NR$^1$—CO— or —CO—NR$^1$; $X^1$ is a divalent hydrocarbyl group having from 1 to about 10 carbon atoms which can contain one or more heteroatoms selected from N, O or S and may be saturated or unsaturated; each R and R$^1$ is independently hydrogen or an aliphatic hydrocarbon group having from 1 to about 4 carbon atoms; each X is independently hydrogen, a hydrocarbyl or hydrocarbyloxy group having from 1 to about 12 carbon atoms, a halogen atom, —NO$_2$, or —C≡N; and n' is zero or one; or any combination of any two or more epoxy resins represented by Formulas I and II;

(b) said monoepoxide compound containing one or more rodlike mesogenic moieties is a compound represented by either the following Formula III

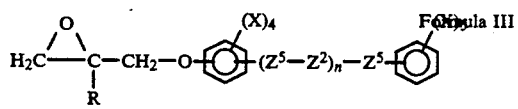

wherein at least about 80 percent of the —(Z$^5$-Z$^2$)$_n$—Z$^5$— linkages and the glycidyl ether groups are in the para position with respect to each other; each R and R$^1$ is independently hydrogen or an aliphatic hydrocarbon group having from 1 to about 4 carbon atoms; each X is independently hydrogen, a hydrocarbyl or hydrocarbyloxy group having suitably from 1 to about 12 carbon atoms, a halogen atom, —NO$_2$, or —C≡N; each Z$^5$ is independently —CR$^1$=CR$^1$—, —CR$^1$=C-R$^1$—CR$^1$=CR$^1$—, —CR$^1$=N—N=CR$^1$—, —CR$^1$=CR$^1$—CO—O—CH$_2$—, —CR$^1$=C-R$^1$—CO—O—CH$_2$—CH$_2$—, —CH$_2$—O—CO—CR$^1$=CR$^1$—, —CH$_2$—CH$_2$—O—CO—CR$^1$=CR$^1$, —CR$^1$=C-R$^1$—CO—O—, —O—CO—CR$^1$=CR$^1$—, —N=N—, —CO—NR$^1$—, —NR$^1$—CO—, —CO—NR$^1$—NR$^1$—CO—, —C≡C—, —C≡C—C≡C—, —CO—S—, —S—CO—, —CR$^1$=N—, —N=CR$^1$—, —CO—O—, —O—CO—, —CR$^1$=CR$^1$—O—CO—CH$_2$—, —CH$_2$—CO—O—CR$^1$=CR$^1$—, —CR$^1$—CR$^1$—O—CO—CH$_2$—CH$_2$—, —CH$_2$—CH$_2$—CO—O—CR$^1$=CR$^1$—, —CH$_2$—CH$_2$—CO—O—, —O—CO—CH$_2$—CH$_2$—, —CO—O—CR$^1$=CR$^1$—, —CR$^1$=C-R$^1$—O—CO—, a direct single bond when n≧1,

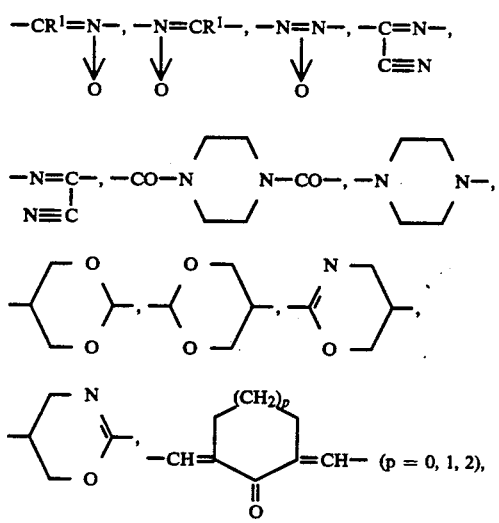

-continued

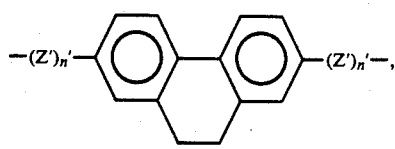

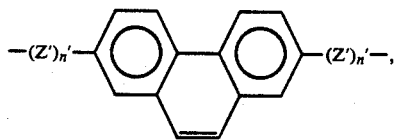

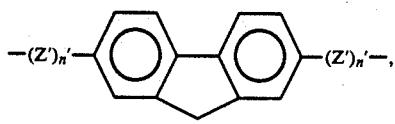

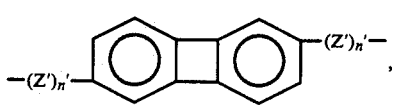

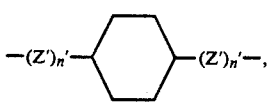

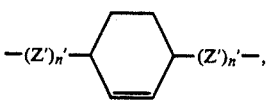

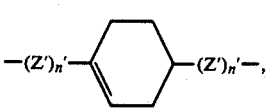

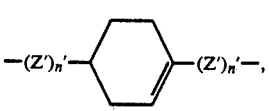

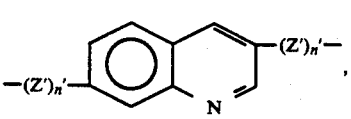

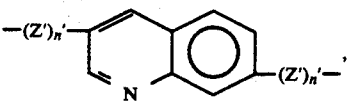

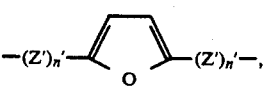

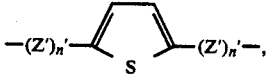

-continued

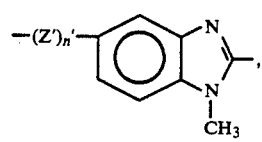

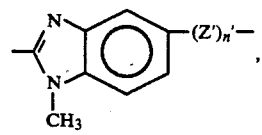

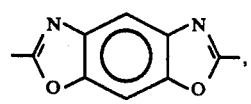

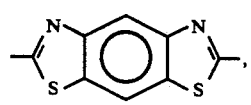

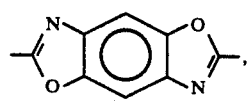

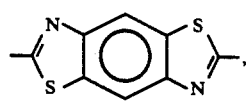

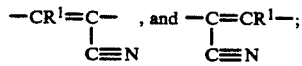

$Z^2$ is a group represented by a cyclic or bicyclic ring system containing from 5 to about 12 carbon atoms and may be cycloaliphatic, polycycloaliphatic, aromatic or a combination thereof; n is zero or two; each $Z'$ is independently a —CO—, —O—CO—, —CO—O—, —CO—NR$^1$—, or —NR$^1$—CO— group; and each n' is independently zero or one; or by the following Formula IV

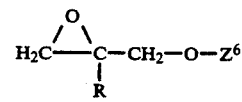 Formula IV wherein $Z^6$ is

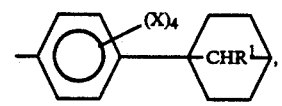

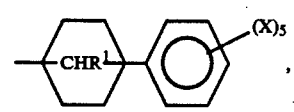

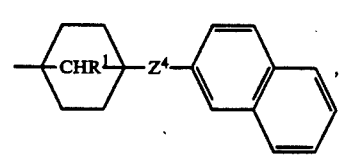

-continued

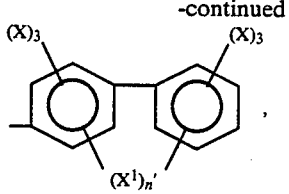

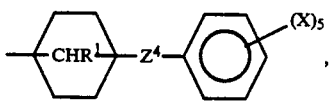

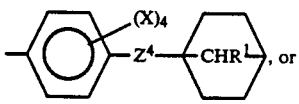

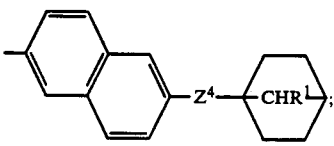

$Z^4$ is —CO—O—, —O—CO—, —NR$^1$—CO— or —CO—NR$^1$—; each R and R$^1$ is independently hydrogen or an aliphatic hydrocarbon group having from 1 to about 4 carbon atoms; each X is independently hydrogen, a hydrocarbyl or hydrocarbyloxy group having from 1 to about 12 carbon atoms, a halogen atom, —NO$_2$, or —C≡N; X$^1$ is a divalent hydrocarbyl group having from 1 to about 10 carbon atoms which can contain one or more heteroatoms selected from N, O or S and may be saturated or unsaturated; and n' is zero or one; any combination of any two or more monoepoxide compounds represented by Formulas III and IV; and (c) component (A) is present in an amount of from about 1 to about 99 percent by weight based upon the combined weight of components (A) and (B) and component (B) is present in an amount of from about 99 to about 1 percent by weight based upon the combined weight of components (A) and (B).

16. A curable composition of claim 15 wherein component (A) is present in an amount of from about 10 to about 80 percent by weight based upon the combined weight of components (A) and (B) and component (B) is present in an amount of from about 90 to about 20 percent by weight based upon the combined weight of components (A) and (B).

17. A curable composition of claim 16 wherein component (A) is present in an amount of from about 10 to about 50 percent by weight based upon the combined weight of components (A) and (B) and component (B) is present in an amount of from about 90 to about 50 percent by weight based upon the combined weight of components (A) and (B).

18. A curable composition of claim 1, 2, 3, 4, 5, 6, 7, 8, 9, 10, 11, 12, 13, 14, 15, 16 or 17 wherein said polyamine containing one or more rodlike mesogenic moieties is represented by the following Formula XIX

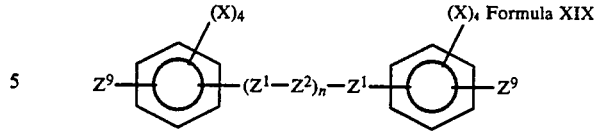

wherein at least about 80 percent of the —(Z$^1$-Z$^2$)$_n$—Z$^1$— linkages and the Z$^9$ groups are in the para position with respect to each other; each R$^1$ is independently hydrogen or an aliphatic hydrocarbon group having from 1 to about 12 carbon atoms; each X is independently hydrogen, a hydrocarbyl or hydrocarbyloxy group having suitably from 1 to about 12 carbon atoms, a halogen atom, —NO$_2$, or —C≡N; each Z$^1$ is independently —CR$^1$=CR$^1$—, —CR$^1$=C-R$^1$—CR$^1$=CR$^1$—, —CR$^1$=N—N=CR$^1$—, —CR$^1$=CR$^1$—CO—O—CH$_2$—, —CR$^1$=C-R$^1$—CO—O—CH$_2$—CH$_2$—, —CH$_2$—O—CO—CR$^1$=CR$^1$—, —CH$_2$—CH$_2$—O—CO—CR$^1$=CR$^1$, —CR$^1$=CR$^1$—CO—O—, —O—CO—CR$^1$=CR$^1$—, —CO—NR$^1$, —NR$^1$—CO—, —CO—NR$^1$—NR$^1$—CO—, —C≡C—, —C≡—C—C≡C—, —N=N—, —CO—S—, —S—CO—, —CR$^1$=N—, —N=CR$^1$—, —CO—CR$^1$=C-R$^1$—, —CR$^1$=CR$^1$—CO—, —CR$^1$=C-R$^1$—O—CO—CH$_2$—, —CH$_2$—CO—O—CR$^1$=CR$^1$, —CR$^1$=CR$^1$—O—CO—CH$_2$—CH$_2$—, —CH$_2$—CH$_2$—CO—O—CR$^1$=CR$^1$—, —CH$_2$—CH$_2$—CO—O—, —O—CO—CH$_2$—CH$_2$—, —CO—O—CR$^1$=CR$^1$—, —CR$^1$=CR$^1$—O—CO—,

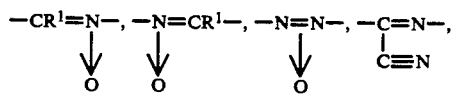

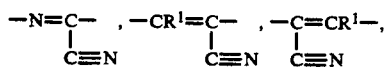

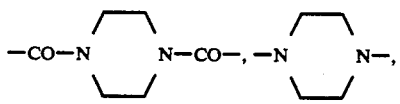

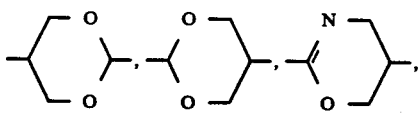

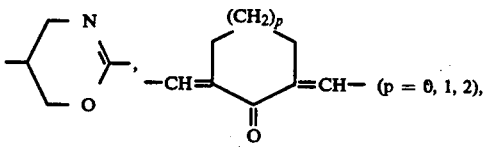

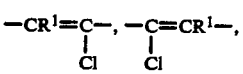

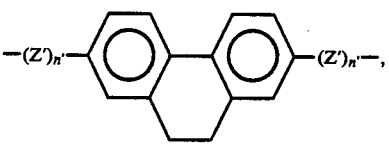

$Z^2$ is a group represented by a cyclic or bicyclic ring system containing from 5 to about 12 carbon atoms and may be cycloaliphatic, polycycloaliphatic, aromatic or a combination thereof; n is 0 to 2; each $Z^9$ is independently a $-NHR^1$, $-O-(CHR^1)_n-CHR^1-NHR^1$, $-NR^1-(CHR^1)_n-CHR^1-NHR^1$, $$-\overset{\overset{O}{\|}}{C}-NR^1-(CHR^1)_n-CHR^1-NHR^1,$$

$$-\overset{\overset{O}{\|}}{C}-O-(CHR^1)_n-CHR^1-NHR^1,$$

$$-O-\overset{\overset{O}{\|}}{C}-(CHR^1)_n-CHR^1-NHR^1 \text{ or}$$

$$-NR^1-\overset{\overset{O}{\|}}{C}-(CHR^1)_n-CHR^1-NHR^1 \text{ group;}$$

each $Z'$ is independently a $-CO-$, $-O-CO-$, $-CO-O-$, $-CO-NR^1-$, or $-NR^1-CO-$ group and each n' independently has a value of zero or one; or the following Formula XX $$Z^9-Z^3-Z^9 \qquad \text{Formula XX}$$

wherein $Z^3$ is

-continued

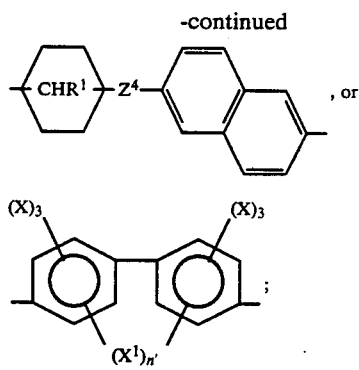

and $Z^4$ is —CO—O—, —O—CO—, —NR$^1$—CO— or —CO—NR$^1$—; $X^1$ is a divalent hydrocarbyl group having from 1 to about 10 carbon atoms which can contain one or more heteroatoms selected from N, O or S and may be saturated or unsaturated; each $R^1$ is independently hydrogen or an aliphatic hydrocarbon group having from 1 to about 4 carbon atoms; each X is independently hydrogen, a hydrocarbyl or hydrocarbyloxy group having suitably from 1 to about 12 carbon atoms, a halogen atom, —NO$_2$, or —C≡N; and n' is zero or one; and $Z^9$ is as hereinbefore defined.

19. A curable composition of claim 18 wherein said curing agent is a 4,4'-diaminostilbene, a 4,4'-diaminobenzanilide, or a combination thereof.

20. The product resulting from curing the curable composition of claim 18.

21. The product of claim 20 wherein said curable composition is oriented prior to and/or during curing of the curable composition.

22. The product of claim 21 wherein said orientations is accomplished by the application of an electric field or magnetic field or drawing and/or shear flow or any combination thereof.

23. The product resulting from curing the curable composition of claim 19.

24. The product of claim 23 wherein said curable composition is oriented prior to and/or during curing of the curable composition.

25. The product of claim 24 wherein said orientation is accomplished by the application of an electric field or magnetic field or drawing and/or shear flow or any combination thereof.

26. The product resulting from curing a curable composition comprising (A) at least one epoxy resin containing one or more rodlike mesogenic moieties, said epoxy resin being represented by the following Formula I

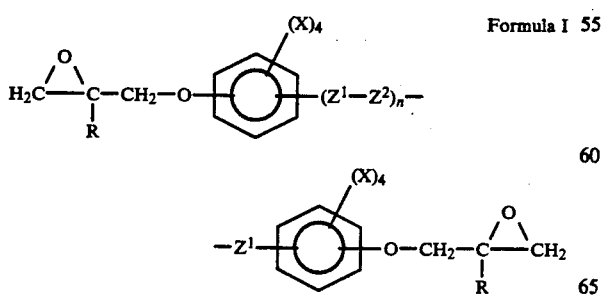

Formula I wherein at least about 80 percent of the —(Z$^1$-Z$^2$)$_n$—Z$^1$— linkages and the glycidyl ether groups are in the para position with respect to each other; each R and $R^1$ is independently hydrogen or an aliphatic hydrocarbon group having from 1 to about 4 carbon atoms; each X is independently hydrogen, a hydrocarbyl or hydrocarbyloxy group having from 1 to about 12 carbon atoms, a halogen atom, —NO$_2$, or —C≡N; $Z^2$, Z', n and n' are as hereinbefore defined claim 1;

with the proviso that:

(a) when n=1, either one of $Z^1$ is selected from the group consisting of —CH=CH—, —N=N—, —CO—S—, —S—CO—, —CH=N—, —N=CH—, —O—CO—, —CO—O— and a direct single bond provided that the other $Z^1$ group is selected from this same group or is selected from a group selected from the group consisting of

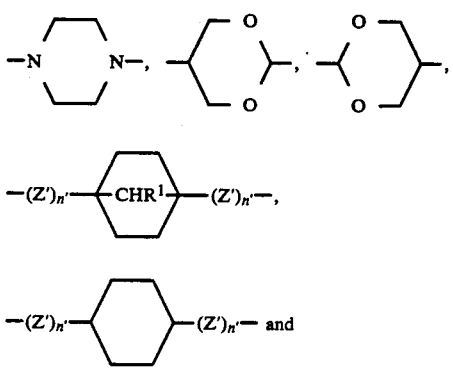

when (i) each n' is zero, or (ii) when one n'=zero and one n'=1 with Z' being —O—CO— or —CO—O— and $R^1$ is a group having only one carbon atom;

(b) when n=2, one or two $Z^1$ groups are independently selected from the group consisting of —CH=CH—, —N=N—, —CO—S—, —S—CO—, —CH=N—, —N=CH—, —O—CO—, —CO—O—, and a direct single bond, provided that the remaining $Z^1$ groups are selected from this group;

(c) when one $Z^1$ is

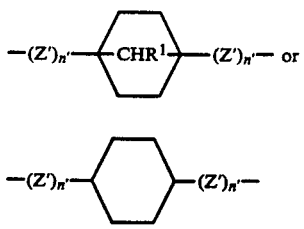

wherein (i) when each n'=1 with each Z' being —O—CO— or —CO—O—, or (ii) when one n'=1 with Z' being —O—CO— or —CO—O— and the other n'=zero resulting in the other Z' being a direct bond and $R^1$ is a group having only one carbon atom, then n must have a value of 1 or 2 and $R^1$ is a group having only one carbon atom; and (B) a curing amount of one or more polyamines containing one or more rodlike mesogenic moieties; and wherein said curing is conducted outside the liquid crystal transition temperature range of said epoxy resin and with the proviso that the epoxy resin and curing agent are not simultaneously the diglycidyl ether of 4,4'-dihydroxyphenylbenzoate and 4,4'-diaminophenylbenzoate, respectively.

27. The product resulting from curing a curable composition comprising (A) at least one epoxy resin containing one or more rodlike mesogenic moieties said epoxy resin being represented by the following Formula II

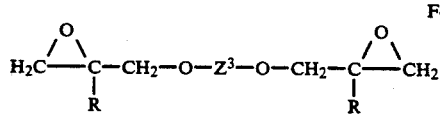
Formula II wherein $Z^3$ is

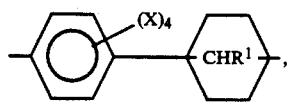

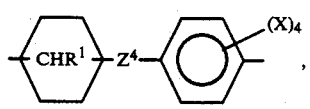

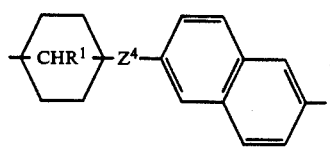

and $Z^4$ is —CO—O— or —O—CO—; each R is independently hydrogen or an aliphatic hydrocarbon group having from 1 to about 4 carbon atoms; $R^1$ is a group having only one carbon atom each X is independently hydrogen, a hydrocarbyl or hydrocarbyloxy group having from 1 to about 12 carbon atoms, a halogen atom, —$NO_2$, or —C≡N; and (B) a curing amount of one or more polyamines containing one or more rodlike mesogenic moieties; and wherein said curing is conducted outside the liquid crystal transition temperature range of said epoxy resin.

28. The product of claim 26 resulting from the application of an electric field or magnetic field or drawing and/or shear flow or any combination thereof prior to and/or during cure.

29. The product of claim 27 resulting from the application of an electric field or magnetic field or drawing and/or shear flow or any combination thereof prior to and/or during cure.

* * * * *

UNITED STATES PATENT AND TRADEMARK OFFICE
CERTIFICATE OF CORRECTION

Page 1 of 2

PATENT NO. : 5,227,452

DATED : July 13, 1993

INVENTOR(S) : Jimmy D. Earls et al.

It is certified that error appears in the above-identified patent and that said Letters Patent is hereby corrected as shown below:

In claim 1, line 63, column 47, "n'-1" should read --n'=1--.

In claim 1, line 17, column 48, "n'-1" should read --n'=1--.

In claim 1, line 18, column 48, "n'-1" should read --n'=1--.

In claim 8, line 62, column 49, "$CR^1$" should read --—$CR^1$--.

In claim 8, line 33, column 54, the third mentioned "$CH_2$-" should be deleted.

In claim 8, line 12, column 58, "or" should read --of--.

In claim 15, line 21, column 61, "-$CR^1$=$CR^1$-," should read --—$CR^1$=$CR^1$-CO—,--.

In claim 15, line 25, column 61, the third mentioned "$CH_2$-" should be deleted.

UNITED STATES PATENT AND TRADEMARK OFFICE
CERTIFICATE OF CORRECTION

PATENT NO. : 5,227,452
DATED : July 13, 1993
INVENTOR(S) : Jimmy D. Earls, et. al.

It is certified that error appears in the above-indentified patent and that said Letters Patent is hereby corrected as shown below:

In claim 22, line 36, column 71, "orientations" should read -- orientation--.

Signed and Sealed this

Twentieth Day of September, 1994

Attest:

BRUCE LEHMAN

Attesting Officer

Commissioner of Patents and Trademarks